US011315669B1

(12) United States Patent
Friedman et al.

(10) Patent No.: US 11,315,669 B1
(45) Date of Patent: Apr. 26, 2022

(54) DYNAMIC GENERATION OF AN ELECTRONIC MEDICAL REPORT SATISFYING MEDICAL REPORTING STANDARDS FROM NON-STANDARDIZED CLINIC NOTES

(71) Applicant: MARYLAND HEALTHCARE CLINICS, LLC, Baltimore, MD (US)

(72) Inventors: Semyon David Friedman, Miami, FL (US); Julia Friedman-Peremel, Annapolis, MD (US); Roman Balakirsky, Timonium, MD (US)

(73) Assignee: MARYLAND HEALTHCARE CLINICS, LLC, Baltimore, MD (US)

( * ) Notice: Subject to any disclaimer, the term of this patent is extended or adjusted under 35 U.S.C. 154(b) by 0 days.

(21) Appl. No.: 17/539,642

(22) Filed: Dec. 1, 2021

(51) Int. Cl.
| | |
|---|---|
| *G16H 15/00* | (2018.01) |
| *G06N 5/02* | (2006.01) |
| *G16H 40/20* | (2018.01) |
| *G16H 10/60* | (2018.01) |

(52) U.S. Cl.
CPC ............ *G16H 15/00* (2018.01); *G06N 5/025* (2013.01); *G16H 10/60* (2018.01); *G16H 40/20* (2018.01)

(58) Field of Classification Search
CPC ........ G16H 15/00; G16H 10/60; G16H 40/20; G06N 5/025
See application file for complete search history.

(56) References Cited

U.S. PATENT DOCUMENTS

| | | | |
|---|---|---|---|
| 2012/0259661 A1* | 10/2012 | Walker ................... | G16H 15/00 705/3 |
| 2021/0398630 A1* | 12/2021 | Sadeghi ................. | G06Q 10/10 |

* cited by examiner

*Primary Examiner* — Maroun P Kanaan
(74) *Attorney, Agent, or Firm* — Knobbe, Martens, Olson & Bear, LLP

(57) ABSTRACT

A system receives patient information from a patient computing device and/or a user computing device via a first network connection. The system further receives clinic notes from a clinic computing system for the generation of an electronic medical report based on a personal injury of the patient via a second network connection. Instead of statically generating a report, the system generates the electronic medical report by obtaining medical reporting standards and identifying rules and/or frameworks that satisfy the medical reporting standards. Further, the system dynamically maps the rules to the frameworks in order to plan the electronic medical report. The system can dynamically build the electronic medical report based on the rules, the frameworks, the patient information, and the clinic notes. After generating the electronic medical report, the system causes display of the electronic medical report via a display of the user computing device.

21 Claims, 13 Drawing Sheets

ACME PHYSICIANS ASSOCIATES
ACME GROUP
183 MAIN STREET, ACME

INITIAL VISIT
RE: PATIENT 1 (RN) SAMPLE
DATE OF INJURY: FEBRUARY 01, 8018
DATE OF VISIT: MARCH 01, 8081

MR. SAMPLE IS A 81-YEAR-OLD RIGHT-HANDED MALE WHO WAS INVOLVED IN AN AUTO ACCIDENT ON FEBRUARY 01, 8018. THE HISTORY, OBTAINED FROM THE PATIENT IS AS FOLLOWS:

MR. SAMPLE WAS A SEAT-BELTED DRIVER IN A MOVING CAR WHICH WAS HIT IN THE FRONT BY ANOTHER CAR. UPON IMPACT HIS BODY MOVED FORWARD AND BACKWARD. HE INJURED HIS CERVICAL SPINE. PERSISTING PAIN IN THE INJURED AREA, POST-TRAUMATIC ANXIETY, A FEAR OF DRIVING, SLEEP DISTURBANCE AND PROBLEMS CONCENTRATING CAUSED MR. SAMPLE TO VISIT THE CLINIC SEEKING MEDICAL ASSISTANCE. THIS SYMPTOM DEVELOPED RIGHT AFTER THE ACCIDENT.

IN SPITE OF HIS INJURY, MR. SAMPLE CONTINUES HIS DAILY ACTIVITIES UNDER DURESS.

Tabs: GENERAL INFORMATION (902A) | ACCIDENT INFORMATION (902B) | MEDICAL HISTORY (902C) | INJURIES (902D) | GENERAL EXAM (902E) | PHYSICAL EXAM (902F)

ACCIDENT INFORMATION (904)

| Field | | | | |
|---|---|---|---|---|
| TYPE OF ACCIDENT: | X AUTO | O MTA | O MOTORCYCLE | O SCOOTER | O BICYCLE | O OTHER |
| CAR ACCIDENT: | | | | |
| WERE YOU: | O DRIVER | O PASSENGER | | |
| ACCIDENT HAPPENED: | O MOVING | O STOPPED | O PARKED | |
| YOU WERE IN A: | O CAR | O SUV | O VAN | O PICK-UP TRUCK | O TAXI | O BUS |
| IT WAS: | O N/A | O YOUR OWN | O PARENT'S | O COMPANY CAR |
| SEAT-BELTED: | O YES | O NO | | |
| VEHICLE TOWED: | O YES | O NO | | |
| AIRBAGS DEPLOYED: | O YES | O NO | | |

POST-ACCIDENT INFORMATION (908)

(906)

| Field | | | |
|---|---|---|---|
| AT THE SCENE, THERE WAS: | O POLICE | O FIRE DEPARTMENT | O AMBULANCE |
| COMPLAINTS: | O NO | O YES | |
| ABLE TO PERFORM WORK: | O HOBBIES | O SPORTS | O DO NOT WORK | O LOST JOB |
| OTHER LIMITATIONS: | O YES | O NO | |
| PAID HOUSEHOLD ASSISTANCE: | O YES | O NO | O DOMESTIC DUTIES |
| RELATIONSHIP ISSUES: | | | |

| Area | Pain Level | Sprain/Strain | Traumatic Injuries | Contusion/Superficial Injury | Bruising | Scars |
|---|---|---|---|---|---|---|
| Occipital Area | Mild | N/A | N/A | Healed | o | o |
| Cervical Spine | Moderate | Improved | N/A | N/A | x | o |
| Thoratic Spine | High | Worsened | The same | N/A | o | o |
| Trapezius Left | Mild | New | N/A | N/A | o | o |
| Trapezius Right | ? | ? | ? | ? | o | o |
| Further Areas? | | | | | | |

FIG. 10

DYNAMIC GENERATION OF AN ELECTRONIC MEDICAL REPORT SATISFYING MEDICAL REPORTING STANDARDS FROM NON-STANDARDIZED CLINIC NOTES

BACKGROUND

Field

Some embodiments of the present disclosure are directed to systems and methods for dynamically generating an electronic medical report and improving the routing of information for the generation of the electronic medical report.

Description

Use of electronic medical records has grown considerably over the last several decades, and has exploded in response to advances in technologies (e.g., upgrades to computing systems and computing technologies). Electronic medical records are digital records and/or clinic notes of medical professionals. The use of electronic medical records allows for users to engage with the electronic medical records in a manner that may not have been previously achievable. For example, computing devices can allow a user to have access to the electronic medical record at any time. The electronic medical record may provide access to the notes of the medical professional and the use of computing devices enables the user to take full advantage of these notes. Further, network-based electronic medical records may enable the users, via computing devices, to receive the electronic medical records and access the electronic medical records on-demand.

SUMMARY

For purposes of this summary, certain aspects, advantages, and novel features of the invention are described herein. It is to be understood that not all such advantages necessarily may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

According to various embodiments, of the present disclosure, a computer-implemented method for generation of an electronic medical report satisfying medical reporting standards from clinic notes with different data formats may include obtaining patient information. The patient information may include one or more key-value pairs. The one or more key-value pairs may identify one or more characteristics of the patient. The computer-implemented may further include obtaining clinic notes from a clinic computing system via an application programming interface. The clinic notes may be associated with the patient. The clinic notes may identify one or more of an incident, a medical treatment, or a medical diagnosis associated with the personal injury of the patient. The clinic notes may include first clinic notes and second clinic notes. The first clinic notes and the second clinic notes may have different data formats and may include a plurality of clinic information. A first data format of the first clinic notes and a second data format of the second clinic notes may be based on one or more hardware components or one or more software components of the clinic computing system. The computer-implemented may further include obtaining, from a user computing device, a request to generate the electronic medical report. The electronic medical report may correspond to the personal injury of the patient. The request to generate the electronic medical report may identify a context of the electronic medical report as the personal injury context. The computer-implemented may further include automatically generating, in real time, the electronic medical report based on obtaining the request to generate the electronic medical report. Further, generating the electronic medical report may include obtaining one or more medical reporting standards based on the context of the electronic medical report. The one or more medical reporting standards may identify one or more standards for generation of the electronic medical report. Generating the electronic medical report may further include dynamically defining one or more frameworks for generation of the electronic medical report based on the one or more medical reporting standards. The one or more frameworks may include frameworks for the electronic medical report. Generating the electronic medical report may further include determining one or more rules from a plurality of rules for the generation of the electronic medical report based on the one or more medical reporting standards. The one or more rules may define how to transform at least a portion of the clinic notes based on the one or more medical reporting standards. Generating the electronic medical report may further include dynamically mapping the one or more rules to the one or more frameworks to generate an electronic medical report structure. Generating the electronic medical report may further include filtering the one or more key-value pairs of the patient information to identify a subset of the characteristics of the patient. Generating the electronic medical report may further include transforming the at least a portion of the clinic notes based on the one or more rules. Generating the electronic medical report may further include dynamically building the electronic medical report based at least in part on the electronic medical report structure, the filtered one or more key-value pairs, and the transformed portion of the clinic notes. The electronic medical report may satisfy the one or more medical reporting standards. The electronic medical report may have a standardized data format. The first clinic notes, the second clinic notes, and the electronic medical report may have different data formats. The computer-implemented may further include storing the electronic medical report in a data store. The data store may store a plurality of electronic medical reports. The computer-implemented may further include providing, to the user computing device via a network, remote or local access to the electronic medical report based on automatically generating and storing the electronic medical report and verifying that an account associated with the user computing device is authorized to access the electronic medical report.

In various embodiments, obtaining the request to generate the electronic medical report may be based on obtaining the clinic notes from the clinic computing system.

In various embodiments, the clinic notes may further include a plurality of clinic notes. The plurality of clinic notes may include the first clinic notes and the second clinic notes. The plurality of clinic computing systems may include the clinic computing system. Obtaining the clinic notes may include obtaining the plurality of clinic notes from the plurality of clinic computing systems. Further, obtaining the plurality of clinic notes from the plurality of clinic computing systems may include obtaining the first clinic notes from a first clinic computing system of the plurality of clinic computing systems. Further, obtaining the plurality of clinic notes from the plurality of clinic computing systems may include obtaining the second clinic notes from a second clinic computing system of the plurality of clinic computing systems. The first clinic computing system and the second clinic computing system may be associated with different clinics. The first clinic computing system and the second clinic computing system may be associated with one or more of different hardware components or different software components.

In various embodiments, dynamically building the electronic medical report based at least in part on the electronic medical report structure, the filtered one or more key-value pairs, and the transformed portion of the clinic notes may include combining the first clinic notes and the second clinic notes using the standardized data format.

According to various embodiments, of the present disclosure, a medical record management system for generation of an electronic medical report for a personal injury of a patient may include a data store configured to store one or more electronic medical reports and an electronic medical record module in communication with the data store. The electronic medical record module may obtain patient information. The patient information may include one or more key-value pairs. The one or more key-value pairs may identify one or more characteristics of the patient. Further, the electronic medical record module may obtain clinic notes from a clinic computing system. The clinic notes may be associated with the patient. The clinic notes may identify one or more of an incident, a medical treatment, or a medical diagnosis associated with the personal injury of the patient. Further, the electronic medical record module may obtain a request to generate the electronic medical report. The electronic medical report may correspond to the personal injury of the patient. Further, the electronic medical record module may generate the electronic medical report based on obtaining the request to generate the electronic medical report. To generate the electronic medical report, the electronic medical record module may obtain one or more medical reporting standards. The one or more medical reporting standards may identify one or more standards for generation of the electronic medical report. Further, to generate the electronic medical report, the electronic medical record module may determine one or more frameworks from a plurality of frameworks based on the one or more medical reporting standards. The one or more frameworks may include frameworks for the electronic medical report. Further, to generate the electronic medical report, the electronic medical record module may determine one or more rules from a plurality of rules based on the one or more medical reporting standards. The one or more rules may include rules for the generation of the electronic medical report. Further, to generate the electronic medical report, the electronic medical record module may dynamically map the one or more rules to the one or more frameworks to generate an electronic medical report structure. Further, to generate the electronic medical report, the electronic medical record module may filter the one or more key-value pairs of the patient information to identify a subset of the characteristics of the patient. Further, to generate the electronic medical report, the electronic medical record module may transform a portion of the clinic notes. Further, to generate the electronic medical report, the electronic medical record module may dynamically build the electronic medical report based at least in part on the electronic medical report structure, the filtered one or more key-value pairs, and the transformed portion of the clinic notes. The electronic medical report may satisfy the one or more medical reporting standards. Further, the electronic medical record module may cause display of the electronic medical report via a user interface of a user computing device.

In various embodiments, the clinic notes may include first clinic notes and second clinic notes. To obtain the clinic notes, the electronic medical record module may obtain the first clinic notes from a first clinic computing system. Further, the electronic medical record module may obtain the second clinic notes from a second clinic computing system. The first clinic computing system and the second clinic computing system may be associated with different clinics.

In various embodiments, the electronic medical record module may verify that a user account associated with the user computing device is authorized to obtain the electronic medical report.

In various embodiments, the electronic medical record module may parse the patient information to identify a subset of the patient information. Further, the electronic medical record module may generate one or more alerts based on the subset of the patient information. Further, the electronic medical record module may configure the one or more alerts to provide one or more indications to a computing device associated with the electronic medical record module.

In various embodiments, the electronic medical record module may parse the patient information to identify a subset of the patient information. Further, the electronic medical record module may generate one or more alerts based on the subset of the patient information. Further, the electronic medical record module may configure the one or more alerts to provide one or more indications to a computing device associated with the electronic medical record module. Further, the electronic medical record module may monitor the patient information. Further, the electronic medical record module may cause display of the one or more indications via a display of the computing device based on monitoring the patient information.

In various embodiments, the electronic medical record module may store the one or more rules with a first identifier of the electronic medical report. Further, the electronic medical record module may store the one or more frameworks with a second identifier of the electronic medical report.

In various embodiments, the one or more rules may include one or more extensible stylesheet language transformation rules.

In various embodiments, the electronic medical report may identify an injury of the patient and one or more of a patient pain level associated with the injury, a type of injury, an area of the injury, or one or more injuries associated with the injury.

In various embodiments, the electronic medical record module may further obtain accident information. The electronic medical report may identify the filtered one or more key-value pairs, the transformed portion of the clinic notes, and a transformed portion of the accident information.

In various embodiments, to dynamically build the electronic medical report based at least in part on the electronic medical report structure, the filtered one or more key-value pairs, and the transformed portion of the clinic notes, the electronic medical record module may combine a first portion of the clinic notes corresponding to a first clinic and a second portion of the clinic notes corresponding to a second clinic.

In various embodiments, the electronic medical record module may generate a patient profile based on obtaining the patient information. Further, the electronic medical record module may select an active clinic from a plurality of clinics based on the patient profile. The active clinic may be associated with the clinic computing system. Further, the electronic medical record module may provide the patient information to the clinic computing system.

In various embodiments, to obtain the patient information, the electronic medical record module may obtain a first subset of the patient information from the user computing device and a second subset of the patient information from a patient computing device.

In various embodiments, the electronic medical record module may perform electronic intake of the patient information and the clinic notes.

In various embodiments, to dynamically build the electronic medical report based at least in part on the electronic medical report structure, the filtered one or more key-value pairs, and the transformed portion of the clinic notes, the electronic medical record module may perform dynamic sentence generation to generate one or more sentences of the electronic medical report based at least in part on the one or more rules and the one or more frameworks.

In various embodiments, to obtain the medical reporting standards, the electronic medical record module may obtain the medical reporting standards from a computing device associated with a medical reporting standards agency.

According to various embodiments, of the present disclosure, a non-transitory computer-readable storage media may include instructions executable by a computing system to obtain patient information. The patient information may include one or more key-value pairs. The one or more key-value pairs may identify one or more characteristics of a patient. Further, the non-transitory computer-readable storage media may include instructions executable by the computing system to obtain clinic notes from a clinic computing system. The clinic notes may be associated with the patient. The clinic notes may identify one or more of an incident, a medical treatment, or a medical diagnosis associated with a personal injury of the patient. Further, the non-transitory computer-readable storage media may include instructions executable by the computing system to obtain a request to generate an electronic medical report. The electronic medical report may correspond to the personal injury of the patient. Further, the non-transitory computer-readable storage media may include instructions executable by the computing system to generate the electronic medical report based on obtaining the request to generate the electronic medical report. To generate the electronic medical report, the non-transitory computer-readable storage media may include further instructions executable by the computing system to obtain one or more medical reporting standards. The one or more medical reporting standards may identify one or more standards for generation of the electronic medical report. Further, the non-transitory computer-readable storage media may include further instructions executable by the computing system to determine one or more frameworks from a plurality of frameworks based on the one or more medical reporting standards. The one or more frameworks may include frameworks for the electronic medical report. Further, the non-transitory computer-readable storage media may include further instructions executable by the computing system to determine one or more rules from a plurality of rules based on the one or more medical reporting standards. The one or more rules may include rules for the generation of the electronic medical report. Further, the non-transitory computer-readable storage media may include further instructions executable by the computing system to dynamically map the one or more rules to the one or more frameworks to generate an electronic medical report structure. Further, the non-transitory computer-readable storage media may include further instructions executable by the computing system to filter the one or more key-value pairs of the patient information to identify a subset of the characteristics of the patient. Further, the non-transitory computer-readable storage media may include further instructions executable by the computing system to transform a portion of the clinic notes. Further, the non-transitory computer-readable storage media may include further instructions executable by the computing system to dynamically build the electronic medical report based at least in part on the electronic medical report structure, the filtered one or more key-value pairs, and the transformed portion of the clinic notes. The electronic medical report may satisfy the one or more medical reporting standards. Further, the non-transitory computer-readable storage media may include instructions executable by the computing system to cause display of the electronic medical report via a user interface of a user computing device.

BRIEF DESCRIPTION OF THE DRAWINGS

The drawings are provided to illustrate example embodiments and are not intended to limit the scope of the disclosure. A better understanding of the systems and methods described herein will be appreciated upon reference to the following description in conjunction with the accompanying drawings, wherein:

FIG. 8 is a pictorial diagram depicting an example electronic medical report according to some embodiments herein.

FIG. 9 is a pictorial diagram depicting an example interface for receiving accident information according to some embodiments herein.

FIG. 10 is a pictorial diagram depicting an example interface for receiving injury information according to some embodiments herein.

DETAILED DESCRIPTION

Figure 1A:
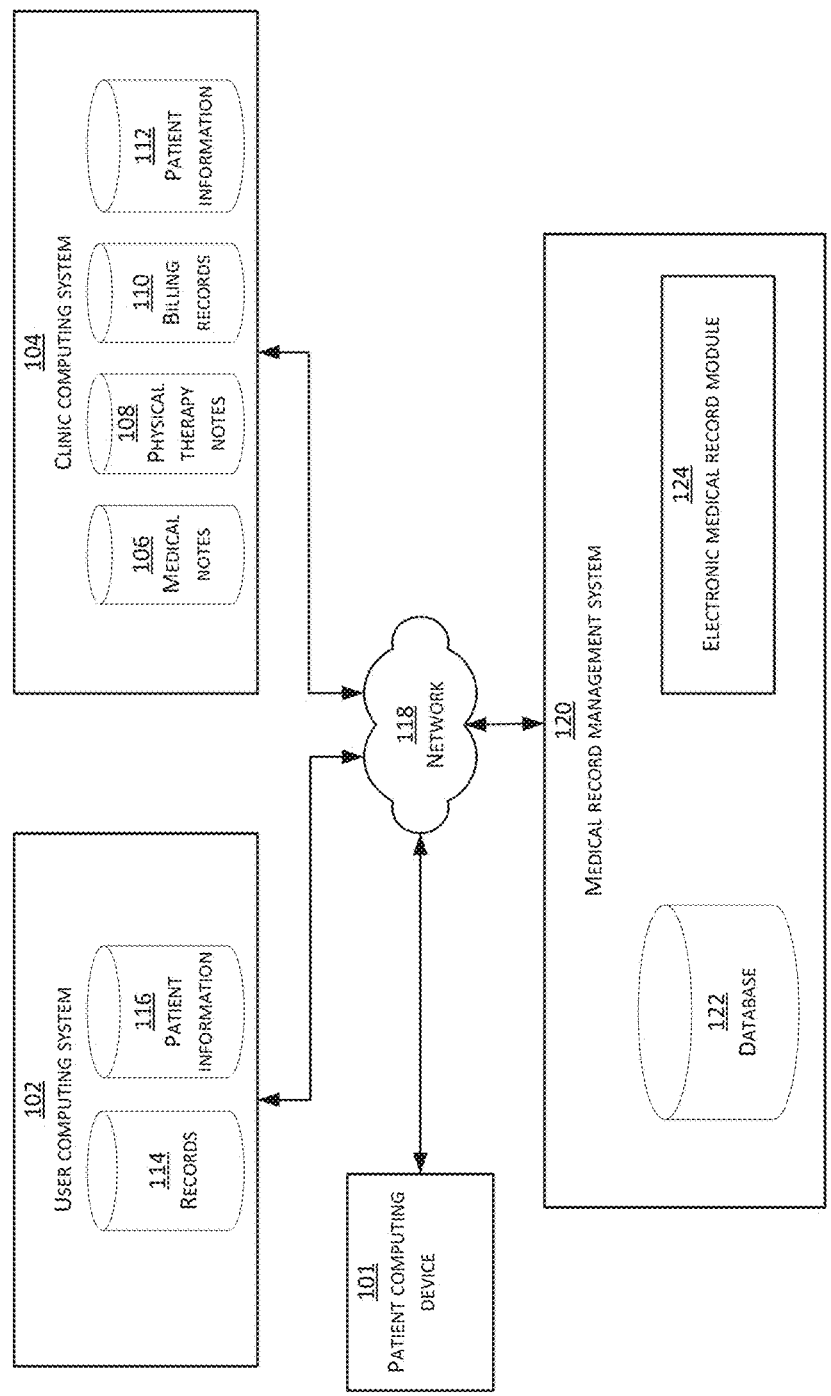
FIG. 1A depicts a schematic diagram of a system including a medical record management system according to some embodiments herein.

Embodiments are described herein according to the following outline:
1.0. General Overview
2.0 System Overview
2.1 Computing Systems and Computing Device
2.2 Network
2.3 Interface
2.4 Database
2.5 Electronic Medical Record Module
3.0. Generation of an Electronic Medical Report
3.1 Alerts Associated with the Electronic Medical Report
3.2 Patient Schedule
3.3 Electronic Intake
4.0 Defining Frameworks and Rules
5.0 Applying Frameworks and Rules
6.0 Electronic Medical Report for User Computing Device
7.0 Example Electronic Medical Report
8.0 User Interface for Receiving Patient Information
9.0 User Interface for Receiving Injury Data
10.0 Computing System 1.0 General Overview Some embodiments herein are directed to an improved system for generating an electronic medical report based on obtained medical records in order to improve the experience of users. The electronic medical report described herein is an example of an electronic medical report that is built and/or generated based on electronic medical records, such as electronic medical records from medical professionals. The electronic medical report is further specific to a particular context (e.g., the personal injury context) and is generated based on the particular context. In some embodiments, the electronic medical report can be a computer-accessible medical report, such as a medical report that is implemented and/or displayed on a mobile computing device (e.g., a tablet, a cell phone, a laptop, etc.). Therefore, the electronic medical report can be implemented and/or displayed on multiple computing devices and users can utilize the computing devices in order to access the electronic medical report and parse data from the electronic medical report.

The electronic medical report can provide information about a personal injury of a patient. Further, the electronic medical report can provide the personal injury information in a format or context particular to personal injury. As will be described, an example system described herein (for example, the medical record management system 120) can be in communication with one or more computing devices to obtain personal injury information associated with the patient. Various medical professionals (e.g., a doctor, a physical therapist, a clinician, a physician, a dentist, a primary care physician, a specialist, etc.) can utilize computing devices to provide personal injury information associated with the patient to the system. Therefore, the system may obtain the personal injury information associated with the patient. Further, the system may obtain the personal injury information in a particular format. For example, the medical professionals may provide the personal injury information in a data format particular to a particular medical professional. Further, the medical professionals may provide the personal injury information in non-standard data formats. Therefore, the system can interact with the medical professionals via computing devices, in order to obtain personal injury information for presentation via an electronic medical report.

The present disclosure generally relates to a medical record management system that obtains the personal injury information and dynamically builds an electronic medical report that enables users to easily parse and use the electronic medical report. The medical record management system may include one or more computing devices, one or more computing modules, a database, etc. The medical record management system may be in communication with an electronic medical record module in order to dynamically generate the electronic medical report. The medical record management system can obtain the personal injury information from computing devices associated with the medical professional and provide the personal injury information to the electronic medical record module in order to dynamically build the electronic medical report. The medical record management system can obtain personal injury information (e.g., medical records) from multiple computing devices (e.g., multiple computing devices associated with multiple different medical professionals). For example, the medical record management system can obtain first personal injury information from a first computing device associated with a physical therapist and second personal injury information from a second computing device associated with a primary care physician. Therefore, the medical record management system can receive personal injury information from multiple computing devices. Based on the personal injury information from multiple computing devices, the medical record management system can dynamically build the electronic medical report that captures personal injury information from the multiple computing devices.

In order to initiate a patient intake process, the medical record management system can receive patient information associated with a particular patient. For example, the patient information may identify the patient, an accident associated with the patient, an urgency level associated with the patient, etc. Based on the patient information, the medical record management system can generate a patient profile and select a particular clinic (e.g., an office associated with a particular medical professional) for the patient. Further, the medical record management system can provide all or a portion of the patient information to the clinic (e.g., a computing device associated with the clinic). The medical record management system may provide the patient information to the clinic in order to generate a patient schedule for the patient. Therefore, the medical record management system can perform a patient intake process and generate a patient profile for the patient in order to identify a patient schedule for the patient.

Based on the patient profile, the medical record management system can further intake personal injury information. For example, the medical record management system may perform electronic intake of clinic notes from multiple clinics (e.g., via multiple clinic computing devices). Based on the patient profile and the personal injury information, the medical record management system can dynamically generate the electronic medical report. In order to dynamically generate the electronic medical report, the medical record management system can obtain medical reporting standards and determine frameworks and rules based on the medical reporting standards. Using the determined frameworks and rules, the medical record management system can dynamically generate the electronic medical report. Further, the medical record management system may use the framework to plan the electronic medical report, invoke the rules based on the patient information, and perform dynamic sentence generation based on the planned electronic medical report and the invoked rules to obtain the electronic medical report. Therefore, the medical record management system can generate the electronic medical report.

Typically, such computing systems may be unable to generate an electronic medical report that is specific to the personal injury context or in a data format specific to the personal injury context. Further, such traditional computing systems may be unable to generate a standardized electronic medical report in a standardized data format from records with a plurality of different content in different data formats. Instead, existing computing systems may provide electronic medical records, as obtained from clinics that provide general information about the patient that may not be specific to the personal injury information, may not be in a standardized data format, and/or may provide undesired information. For example, the electronic medical records may include information that is irrelevant to the personal injury context (e.g., information associated with an unrelated disease or injury). Instead, the general electronic medical records may provide information associated with the patient that may or may not be associated with the personal injury context. Therefore, the electronic medical records may be extensive and/or irrelevant. In the personal injury context, it may be desirable to monitor the type of information, the data format of the information, and the amount of information in the electronic medical report. Parsing the electronic medical record to obtain the relevant information can be inefficient and time consuming. For example, where a patient is associated with multiple electronic medical records (e.g., 10 electronic medical records), it may be inefficient and time consuming to individually parse each electronic medical records. Further, providing the electronic medical records to users may lead to inaccuracies as relevant personal injury information may be missed by the users. Traditional computing systems may be limited to providing the electronic medical records and may not be able to provide an indication of how to parse the electronic medical records. For example, traditional computing systems may not highlight or focus an area of the electronic medical record that pertains to the personal injury context. As traditional computing systems may not be aware that the user desires the personal injury information, traditional computing systems may be unable to provide specific information associated with the personal injury context. Further, this can introduce a delay in the implementation and/or execution of actions based on the electronic medical record. As some actions may be time-sensitive, it may be disadvantageous to provide general electronic medical records that are not specific to the personal injury context. Further, the use of such a traditional computing system can increase memory demands and processing usage by the user computing devices.

The disclosed medical record management system addresses these challenges, among others, by (1) obtaining patient information; (2) dynamically generating electronic medical reports that are specific to the personal injury context; (3) parsing patient information to generate alerts; (4) managing the alerts; and (5) causing presentation of the dynamically generated electronic medical reports. This process may not be capable of being performed mentally as the human mind may not be equipped to parse multiple electronic medical records to identify personal injury information and dynamically generate an electronic medical report that identifies the personal injury information and is specific to the personal injury context.

For purposes of this disclosure, the term "client," "user," and "customer" may each refer to a person that is operating a computing device in order to access the electronic medical report. For purpose of this disclosure, the term "patient" can refer to a person for which the electronic medical reports are providing data. For example, the electronic medical report may provide personal injury data about the patient.

2.0 System Overview

FIG. 1A depicts a schematic diagram of a system 100A including a medical record management system 120 according to some embodiments herein. In the illustrated embodiment, the system 100A includes one or more patient computing devices 101, one or more user computing systems 102, one or more clinic computing systems 104, a network 118, and a medical record management system 120. Any one or any combination of the components shown and described in FIG. 1A can each be implemented using one or more computing devices, such as, but not limited to one or more servers, processors, computing devices, virtual machines, etc., and communicate via the network 118 for generation of the electronic medical report. The network 118 can be a local area network (LAN) or a wide area network (WAN), such as the Internet.

2.1 Computing Systems and Computing Devices

The one or more patient computing devices 101, the one or more user computing systems 102, the one or more clinic computing systems 104, and the medical record management system 120 may include one or more computing systems or computing devices that can include any network-equipped computing device, for example desktop computers, laptops, smartphones, tablets, and the like.

The one or more patient computing devices 101 may include one or more computing devices associated with a patient. The patient may utilize the one or more patient computing devices 101 to provide patient information to the clinic computing system 104 and/or the medical record management system 120. Further, the one or more patient computing devices 101 may include one or more computing devices associated with a particular clinic and utilized by the patient to provide patient information.

The one or more user computing systems 102 may include one or more computing systems associated with a user. The user may utilize the one or more user computing systems 102 to receive and parse the electronic medical report.

The one or more clinic computing systems 104 may include one or more computing systems associated with a particular clinic. The clinic (e.g., a dental clinic, a physical therapy clinic, a medical clinic, etc.) may utilize the one or more clinic computing systems 104 to receive patient information and provide clinic notes (e.g., electronic medical records) to the medical record management system 120. The clinic notes may identify treatment or diagnosis of the patient in a data format particular to the particular clinic.

The medical record management system 120 may include one or more computing systems for the dynamic generation of the electronic medical report. Further, the medical record management system 120 may provide the dynamically generated electronic medical report to the one or more user computing systems 102.

2.2 Network

As illustrated in FIG. 1A, the one or more patient computing devices 101, the one or more user computing systems 102, the one or more clinic computing systems 104, and the medical record management system 120 communicate over the network 118. The network 118 can include any appropriate network, including an intranet, the Internet, a cellular network, a local area network or any other such network or combination thereof. In the illustrated embodiment, the network 118 is the Internet. Protocols and components for communicating via the Internet or any of the other aforementioned types of communication networks are known to those skilled in the art of computer communications and thus, need not be described in more detail herein.

2.3 Interface

The medical record management system 120 may communicate with an interface (e.g., cause an interface to be displayed) associated with the user computing system 102. The interface can be an application programming interface ("API"). The medical record management system 120 may communicate with the interface to enable (e.g., cause) display of the electronic medical report. In some embodiments, the medical record management system 120 may communicate the electronic medical report separately or may provide a uniform resource identifier ("URI") (e.g., a uniform resource locator ("URL")) that enables the user computing system 102 to access the electronic medical report.

2.4 Database

Each of the patient computing device, the user computing system 102, the clinic computing system 104, and/or the medical record management system 120 may be associated with (e.g., may access) a database. For example, the medical record management system 120 may be associated with and/or in communication with database 122. The medical record management system 120 may generate and store the electronic medical report in the database 122. Further, the medical record management system 120 may store, in the database 122, information for the generation of the electronic medical report (e.g., patient information (patient data), particular frameworks, particular rules, etc.). In some embodiments, the medical record management system 120 may access the information for the generation of the electronic medical report from a remote system and/or a remote database.

Further, the user computing system 102 may be associated with and/or in communication with a database. The database may store patient information 116 and/or records 114. For example, the patient information 116 may include information associated with the patient and/or the personal injury (e.g., the date of the accident, the type of accident, a patient statement, etc.). Further, the records 114 may include information associated with any interactions between the patient and the user (e.g., payment information).

The clinic computing system 104 may also be associated with and/or in communication with a database. The database may store clinic notes (e.g., medical notes 106 and/or physical therapy notes 108), billing records 110, and patient information 112. It will be understood that the database may include any clinic notes. For example, if the clinic is a physical therapy clinic, the database may include physical therapy notes (e.g., a physical therapy electronic medical record) and, if the clinic is a dental clinic, the database may include dental notes (e.g., a dental electronic medical record).

2.5 Electronic Medical Record Module

In order to generate the electronic medical report, the medical record management system 120 may include an electronic medical record module 124. The electronic medical record module 124 may receive one or more of the patient information 112 and/or 116, the physical therapy notes 108, the medical notes 106, and/or any additional patient information or clinic notes. Further, the electronic medical record module 124 may identify particular framework(s) and particular rule(s) for the dynamic generation of the electronic medical report. The electronic medical record module 124 can utilize the identified framework(s), the identified rule(s), the clinic notes, and the patient information to dynamically generate the electronic medical report. Based on dynamically generating the electronic medical report, the medical record management system 120 can store the electronic medical report in a database 122 for provisioning to a user computing system 102 (e.g., in response to a request from a user of the user computing system 102). Further, the medical record management system may automatically generate, in real time, the electronic medical report based on obtaining the request to generate the electronic medical report from a user computing system 102 (e.g., a user computing device). The request to generate the electronic medical report may identify a context of the electronic medical report as the personal injury context.

3.0 Generation of an Electronic Medical Report

The medical record management system can (e.g., via the electronic medical record module) dynamically (and automatically) generate an electronic medical report and identify various alerts associated with the electronic medical report. Aspects of this disclosure relate to the generation of the electronic medical report based on obtained patient information that is particular to the medical context (e.g., the personal injury context). The medical record management system may also receive clinic notes and dynamically generate the electronic medical report based on the obtained patient information and the clinic notes. Further, based on the generated electronic medical report, the medical record management system can parse the patient information to identify particular alerts associated with the patient information. Based on the identified alerts, the medical record management system may then receive a subset of the alerts. Accordingly, the medical record management system may dynamically generate the electronic medical report and receive various alerts.

Figure 1B:
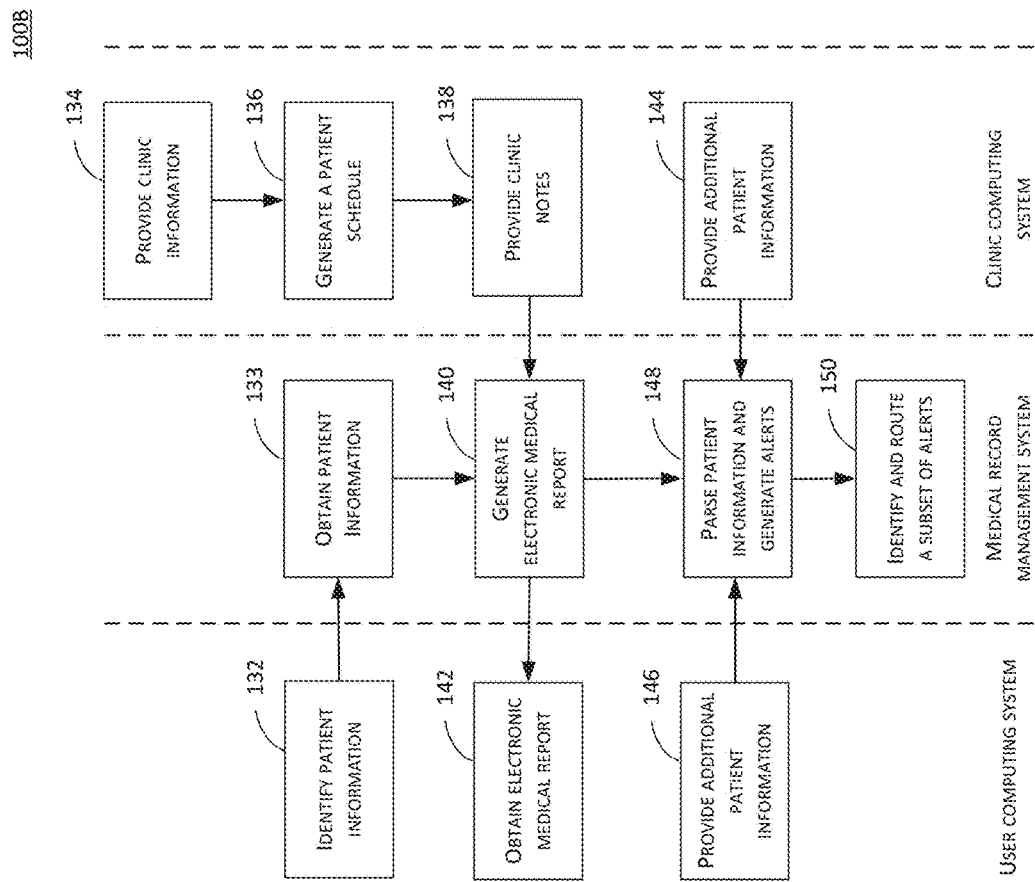
FIG. 1B illustrates an example flowchart of a method for generating electronic medical reports and receiving alerts according to some embodiments herein.

FIG. 1B illustrates an example flowchart of a method 100B for generating the electronic medical report and receiving a subset of alerts according to some embodiments herein. In some embodiments, the user computing system can identify patient information at 132. The patient information may include any information about the patient. For example, the patient information may include information associated with the patient and provided by the patient to the user (e.g., biographical information associated with the patient, information associated with a personal injury, etc.). Further, the patient information may include information that is irrelevant to the electronic medical report and information that is relevant to the electronic medical report. For example, the patient information may include information that is irrelevant to the electronic medical report such as insurance information associated with the patient, an "in case of emergency" contact for the patient, etc. Therefore, the user computing system can identify the patient information.

In some embodiments, the medical record management system can obtain the patient information at 133. The medical record management system may obtain the patient information from the user computing system. In some embodiments, the medical record management system can obtain the patient information in real-time. In other embodiments, the medical record management system can obtain the patient information periodically. Therefore, the medical record management system can receive the patient information from the user computing system.

In some embodiments, the clinic computing system can provide clinic information at 134. The clinic computing system can identify that the patient has been associated with or linked to the particular clinic. Based on this identification, the clinic computing system can provide the clinic information.

In some embodiments, the clinic computing system can generate a patient schedule at 136. The clinic computing system may generate the patient schedule based on the clinic information and determining that the patient is associated with the clinic. The patient schedule may include one or more appointments for the patient at the clinic. Further, the clinic computing system may route the patient schedule to a patient computing device, the user computing device, and/or the medical record management system. Therefore, the clinic computing system can generate the patient schedule.

In some embodiments, the clinic computing system can provide clinic notes at 138. Based on the patient schedule, clinic notes can be generated using the clinic computing system. For example, a patient appointment may be conducted and, based on the patient appointment, clinic notes can be generated using the clinic computing system. Further, the clinic notes may identify medical treatment, medical diagnosis, etc. of the patient based on the patient. Further, the clinic notes may include information that is irrelevant to the electronic medical report and information that is relevant to the electronic medical report. For example, the clinic notes may include information that is irrelevant to the electronic medical report such as notes of the medical professional that are determined to not be relevant. The clinic computing device may provide the clinic notes to the electronic medical record management system.

In some embodiments, the medical record management system can generate an electronic medical report at 140. As discussed below, the medical record management system can utilize the clinic notes and the patient information to generate the electronic medical report. Further, the medical record management system can generate the electronic medical report to include all or a portion of the clinic notes and/or the patient information in a particular format related to the personal injury context. For example, the medical record management system can parse the patient information and/or the clinic notes to identify at least a portion of the patient information and/or the clinic notes that are relevant to the electronic medical report (e.g., related to the personal injury context). Therefore, the medical record management system can generate the electronic medical report.

In some embodiments, the user computing system can obtain the electronic medical report at 142. The user computing system may obtain the electronic medical report from the medical record management system. Further, the user computing system may obtain the electronic medical report in response to a prompt by the user computing system. In some embodiments, the user computing system may obtain the electronic medical report in response to the generation by the medical record management system.

3.1 Alerts Associated with the Electronic Medical Report

Based on the generated electronic medical report (e.g., the patient information and/or the clinic notes associated with the electronic medical report), the medical record management system may generate and/or initiate one or more alerts. The one or more alerts may be based on the generated electronic medical report and may identify information associated with the electronic medical report. For example, the alerts may identify actions by the user, the patient, or the clinic. The medical record management system may further provide one or more dashboards based on generating the electronic medical report. For example, the medical record management system may identify a dashboard for presentation of electronic medical reports by prioritizing and assigning the electronic medical reports into different categories (e.g., based on business requirements) for review by a reviewer, a dashboard for gathering clinic notes (e.g., x-ray notes that require authorization), a dashboard for providing electronic medical reports for review and transmission, a dashboard for transmission of other records (e.g., bills), a dashboard for providing patient information for review by the user, or any other dashboards.

In some embodiments, the clinic computing system can provide additional patient information at 144. The clinic computing system may provide the additional patient information to the medical record management system. The additional patient information may include any information associated with the patient. For example, the additional patient information may be based on monitoring the electronic medical report, subsequent clinic notes, updated requirements, etc.

In some embodiments, the user computing system can provide additional patient information at 146. The user computing system may provide the additional patient information to the medical record management system. As discussed above, the additional patient information may include any information associated with the patient. Therefore, the clinic computing system and the user computing system may provide additional patient information to the medical record management system.

In some embodiments, the medical record management system can parse the patient information (e.g., the patient information and any additional patient information) and generate alerts at 148. The medical record management system may generate alerts that identify a status of the patient information or any other information associated with the patient. For example, the alerts can identify changes to the patient information, incomplete patient information, requests from the user, changes to information associated with the user, issues with generation of the electronic medical report, a status of the electronic medical report, a verification of records, or any other alerts. Therefore, the medical record management system can parse the patient information to generate the alerts.

In some embodiments, the medical record management system can identify and route a subset of the alerts at 150. The medical record management system may identify alerts with particular statuses. For example, alerts that are activated or that meet particular qualifications. Based on identifying the particular alerts, the medical record management system can route the alerts to particular computing devices (e.g., particular computing devices within a medical record management group, the user computing device, etc.). Therefore, the medical record management system can identify and route the subset of the alerts.

3.2 Patient Schedule

In order to generate the electronic medical report, the medical record management system may also provide patient information to a clinic computing system. By providing the patient information to a clinic computing system (e.g., a clinic selected by the medical record management system), the medical record management system can facilitate the generation of a patient schedule for the patient. Further, the medical record management system can facilitate the provision of the electronic medical report to the patient (e.g., via the patient computing device). Therefore, the medical record management system can facilitate the generation of a patient schedule in order to obtain clinic notes for the generation of the electronic medical report.

Figure 2:
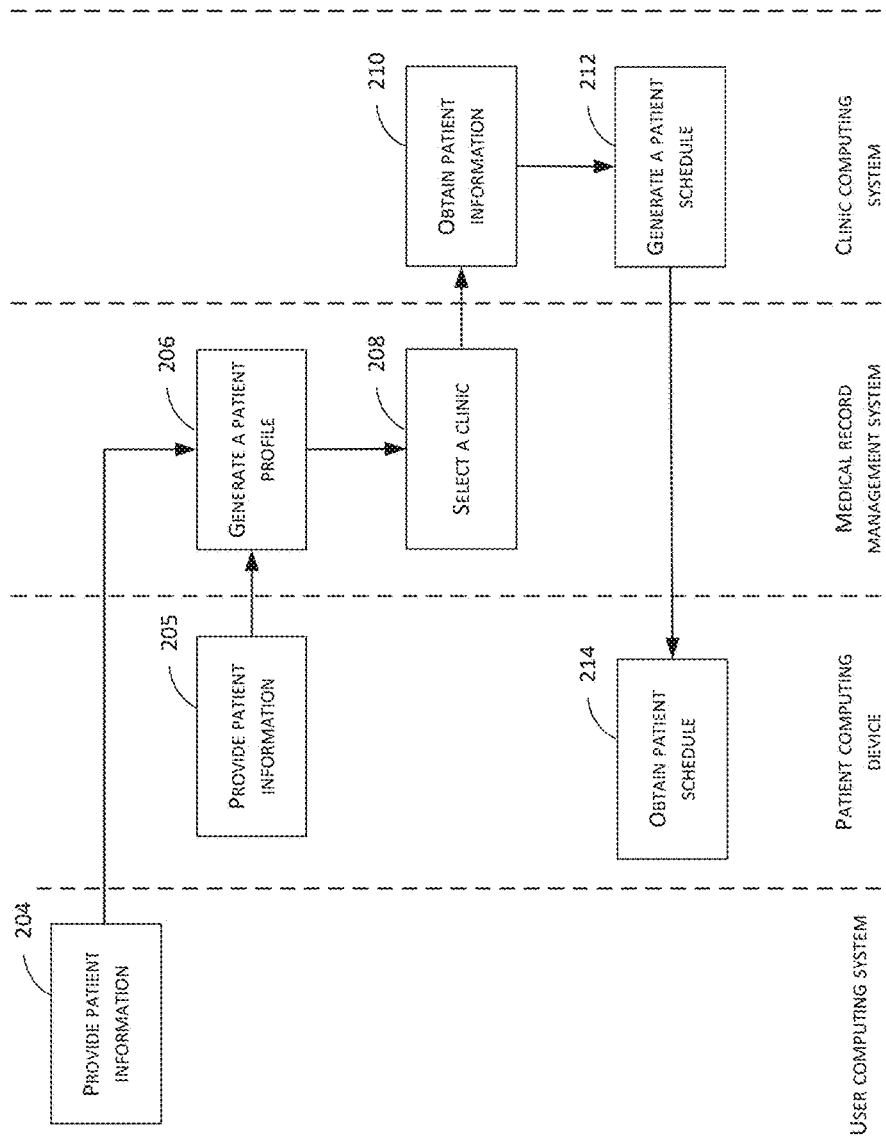
FIG. 2 illustrates an example flowchart of a method for generating a patient schedule according to some embodiments herein.

FIG. 2 illustrates an example flowchart of a method 200 for generating a patient schedule according to some embodiments herein. In some embodiments, the user computing system can provide patient information at 204. The user computing system may provide the patient information to the medical record management system. As discussed above, the patient information may include any information associated with the patient. Therefore, the user computing system can provide the patient information to the medical record management system.

In some embodiments, the patient computing device can provide patient information at 205. The patient computing device may provide the patient information to the medical record management system. In some embodiments, the patient computing device, the user computing system, or a separate computing device may provide the patient information.

In some embodiments, the medical record management system can generate a patient profile at 206. The medical record management system may generate the patient profile based on patient information obtained from the patient computing device, the user computing system, or a separate computing device. The medical record management system may generate the patient profile by linking the patient information to a particular patient identifier (e.g., a social security number) that may be included in the patient information. Therefore, the medical record management system can generate the patient profile.

In some embodiments, the medical record management system can select a clinic (e.g., an active clinic) at 208. The medical record management system can select the active clinic from a plurality of clinics. The medical record management system may select the clinic based on the patient profile and/or the obtained patient information. For example, the patient information may identify an injury of the patient and the medical record management system may identify a clinic associated with that injury. Further, the patient information may indicate a preference for a particular clinic. Therefore, the medical record management system may select the clinic.

In some embodiments, the clinic computing system can obtain the patient information at 210. The medical record management system may provide the patient information to the clinic computing system. Further, the medical record management system may provide the patient information to the clinic computing system based on selecting the clinic associated with the clinic computing system. The medical record management system may provide all or a portion of the patient information provided to the medical record management system to the clinic computing system. Therefore, the clinic computing system can obtain the patient information.

In some embodiments, the clinic computing system may generate the patient schedule at 212. The clinic computing system may utilize the patient information to generate the patient schedule. For example, the clinic computing system can parse the patient information to identify a particular injury of a patient, base information associated with the patient, prior treatment of the patient, a preference for a treatment type and/or a treatment schedule. The clinic computing system may generate the patient schedule based on the identified patient information.

In some embodiments, the patient computing device can obtain the patient schedule at 214. The patient computing device can obtain the patient schedule from the clinic computing system. For example, the patient computing device can obtain the patient schedule in response to the generation of the patient schedule by the clinic computing system.

3.3 Electronic Intake

The medical record management system may facilitate the generation of a patient schedule that is associated with a particular patient and multiple clinics. Based on the patient schedule associated with multiple clinics, the medical record management system can perform electronic intake in order to obtain the clinic notes from each clinic. Based on the obtained clinic notes, the medical record management system may dynamically generate the electronic medical report.

Figure 3:
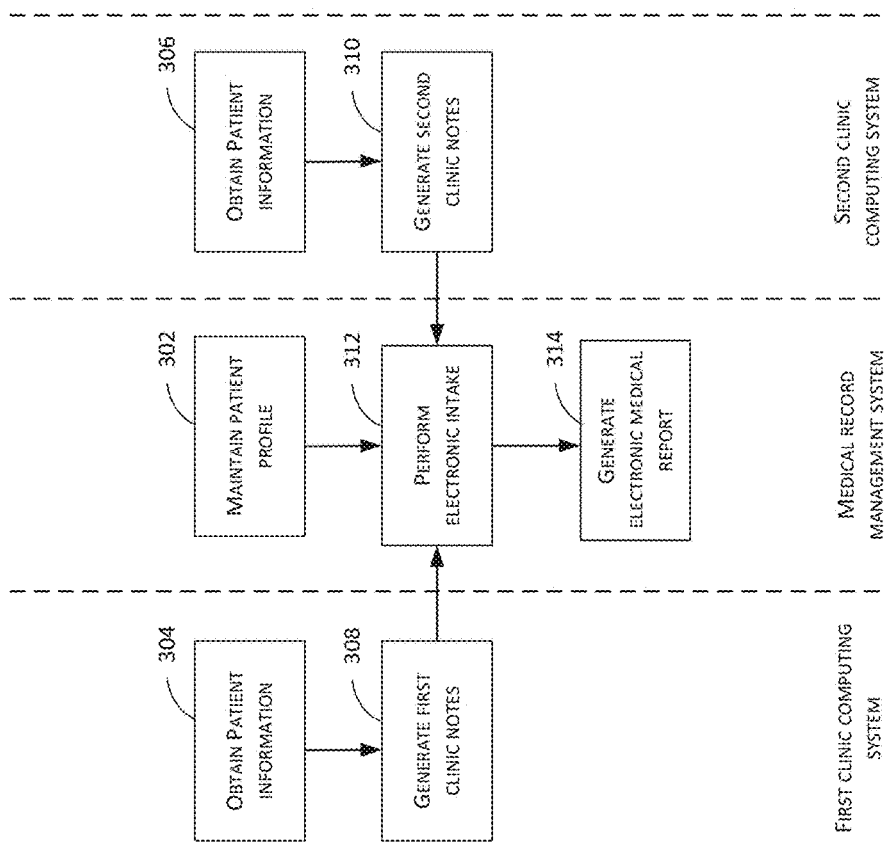
FIG. 3 illustrates an example flowchart of a method for generating an electronic medical report according to some embodiments herein.

FIG. 3 illustrates an example flowchart of a method 300 for generating an electronic medical report based on clinic notes from multiple clinics according to some embodiments herein. In some embodiments, the medical record management system can maintain a patient profile at 302. As discussed above, the patient profile may link the patient information of the patient to a particular patient identifier. Further, the patient profile may link previous clinic notes to the patient. The medical record management system may maintain the patient profile based on a registration, by the patient or the user, of the patient with the medical record management system. Therefore, the medical record management system may maintain the patient profile.

In some embodiments, the first clinic computing system can obtain patient information at 304. The first clinic computing system may obtain the patient information from a patient computing device, the medical record management system, an intake computing device associated with the first clinic, or any other computing device. As discussed above, the first clinic computing system may receive the patient information to generate a first patient schedule for the patient. Therefore, the first clinic computing system can obtain the patient information.

In some embodiments, the second clinic computing system can obtain patient information at 306. The second clinic computing system may obtain the patient information from a patient computing device, the medical record management system, an intake computing device associated with the first clinic, or any other computing device. In some embodiments, the first clinic computing system and the second clinic computing system may obtain different patient information. In other embodiments, the first clinic computing system and the second clinic computing system may obtain the same patient information. The second clinic computing system may receive the patient information to generate a second patient schedule for the patient. Therefore, the second clinic computing system can obtain the patient information.

In some embodiments, the first clinic computing system can generate first clinic notes at 308. The first clinic notes may be based on the provided patient information. The first clinic notes may include a plurality of notes or records associated with a first patient appointment at a first clinic associated with the first clinic computing system. The first clinic notes may include information associated with the first patient appointment. The first clinic notes may be entered by a first medical professional to the first clinic computing system and provided to the medical record management system. Therefore, the first clinic computing system can generate the first clinic notes and provide the first clinic notes the medical record management system.

In some embodiments, the second clinic computing system can generate second clinic notes at 310. The second clinic notes may be based on the provided patient information. The second clinic notes may include a plurality of notes or records associated with a second patient appointment at a second clinic associated with the second clinic computing system. The second clinic notes may include information associated with the second patient appointment. The second clinic notes may be entered by a second medical professional to the second clinic computing system and provided to the medical record management system. In some embodiments, the first clinic computing system and the second clinic computing system may be associated with the same clinic (e.g., the first clinic computing system and the second computing system may be the same clinic computing system). In other embodiments, the first clinic computing system and the second clinic computing system may be different clinic computing systems and/or may be associated with different clinics. Therefore, the second clinic computing system can generate the second clinic notes and provide the second clinic notes to the medical record management system.

In some embodiments, more, less, or different clinic computing systems may generate and provide clinic notes to the medical record management system. Each clinic computing system may be associated with a different clinic. In some embodiments, clinic computing systems may each provide multiple clinic notes. For example, a particular clinic computing system may provide first clinic notes corresponding to a first patient appointment and second clinic notes corresponding to a second patient appointment. Each of the clinic notes may include a plurality of clinic information. Further, each of the clinic notes may have different data formats. For example, each of the clinic notes may have a particular general arrangement but the clinic information within the clinic notes may have different data formats. Further, the data format of the clinic notes may be based on the clinic computing system producing the clinic notes. For example, the first clinic notes associated with a first clinic computing system may have a first data format and the second clinic notes associated with a second clinic computing system may have a second data format. Further, the first data format and the second data format may be based on hardware components (e.g., memory, processors, etc.) and/or software components (e.g., the software used for the generation of the clinic) of the associated clinic computing system. For example, a first clinic computing system may produce clinic notes with a first data format based on software associated with the first clinic computing system and a second clinic computing system may produce clinic notes with a second data format based on software associated with the second clinic computing system. Further, the data format of the clinic notes may be based on the timing of the patient appointment. For example, clinic notes corresponding to a first patient appointment (e.g., an initial patient appointment) may have a different data format from clinic notes corresponding to a second patient appointment (e.g., a subsequent patient appointment). In some embodiments, the first clinic notes and the second clinic notes may have the same data format. For example, the first clinic notes generated by the first clinic computing system and the second clinic notes generated by the second clinic computing system may have the same data format. In some embodiments, the medical record management system may obtain the clinic notes via a graphical user interface, an application programming interface, etc. For example, the medical record management system may obtain the first clinic notes from the first clinic computing system via a first graphical user interface and the second clinic notes from the second clinic computing system via a second graphical user interface.

In some embodiments, the medical record management system can perform electronic intake at 312. The medical record management system may perform electronic intake in order to obtain the first clinic notes and the second clinic notes. Further, the medical record management system may perform electronic intake in order to link the first clinic notes, the second clinic notes, and the patient profile (e.g., based on a patient profile). Therefore, the medical record management system can perform electronic intake of the clinic notes generated by multiple clinic computing systems and associate these notes with the patient information.

In some embodiments, the medical record management system can generate an electronic medical report at 314. As discussed below, the medical record management system can generate the electronic medical report based on the obtained clinic notes and patient information associated with the patient. The medical record management system can provide the generated electronic medical report to a user computing device. The electronic medical report may have a standardized data format based on the medical reporting standards. Further, each of the clinic notes and the electronic medical report may have different data formats and generating the electronic medical report may include standardizing the clinic notes (the clinic notes having non-standardized data formats) into a standardized data format for the electronic medical report.

4.0 Defining Frameworks and Rules

The medical record management system may include an electronic medical record module that can generate an electronic medical report for users based on defined frameworks (e.g., templates, report templates, report frameworks, report structures, etc.) and rules. Users often require summarizations and/or reports that include information associated with a patient. For example, a user may require a summarization of a patient's visits to a medical professional. The notes from the patient's visits may be captured in a non-standard form. For example, the notes from each visit may be captured in a particular format, style, context, etc. based on the particular medical professional associated with the particular visit. In order to standardize the format of the notes from each visit and compile the notes for generation of an electronic medical report, the medical record management system can obtain or identify frameworks and rules for the generation of the electronic medical report. Prior to identifying frameworks and rules for the generation of the electronic medical report, the medical record management system may identify particular frameworks and rules that are eligible to be utilized for the generation of the electronic medical report. For example, the medical record management system may identify frameworks and rules based on medical reporting standards. Further, the medical record management system may utilize particular frameworks and rules of the identified frameworks and rules to generate the electronic medical report. The frameworks and the rules may be particular to and/or based on a personal injury context. Accordingly, the medical record management system can identify particular rules and frameworks based on the medical reporting standards.

Figure 4:
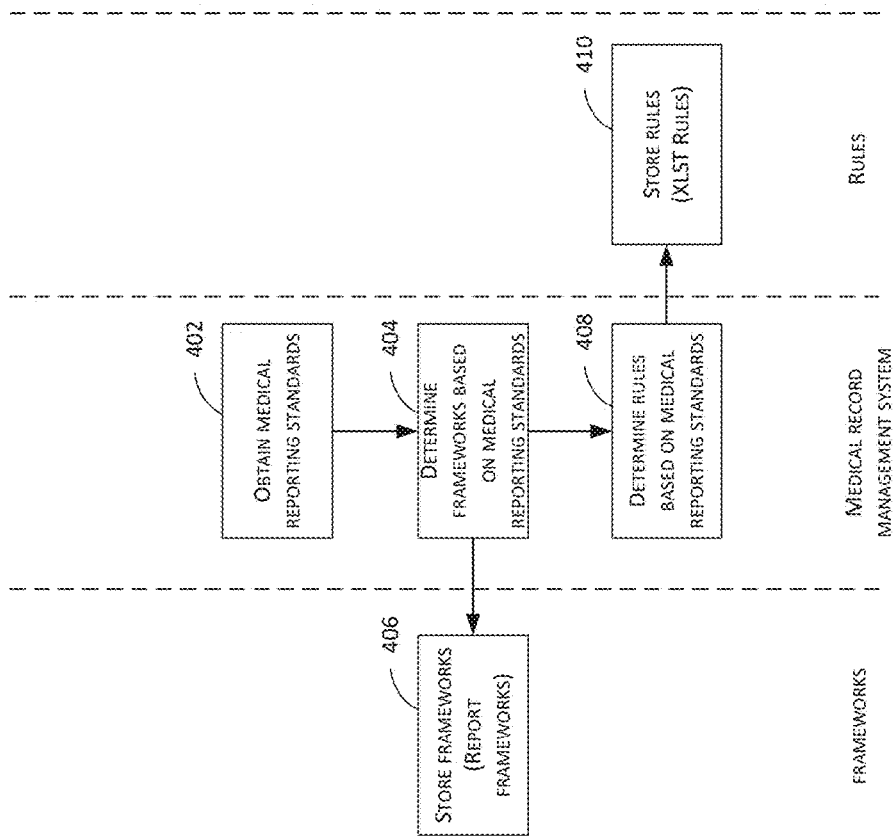
FIG. 4 illustrates an example flowchart of a method for determining rules and frameworks based on medical reporting standards according to some embodiments herein.

FIG. 4 illustrates an example flowchart of a method 400 for receiving medical reporting standards and determining frameworks and rules for the generation of the electronic medical report according to some embodiments herein. In some embodiments, the medical record management system can obtain medical reporting standards at 402. The medical record management system may obtain the medical reporting standards based on the context of the electronic medical report (e.g., the personal injury context). Further, the medical reporting standards may be particular to the personal injury context. The medical record management system can obtain the medical reporting standards from a third party computing device. For example, the medical record management system may obtain the medical reporting standards from a computing device associated with a standards agency. Further, the medical record management system can obtain the medical reporting standards and determine how to apply the medical reporting standards. For example, the medical record management system can obtain the medical reporting standards and identify one or more rules for applying the medical reporting standards. The rules for applying the medical reporting standards may be user defined, system defined, or otherwise defined for the system. For example, the rules for applying the medical reporting standards may identify how to determine framework(s) and/or rule(s) based on the medical reporting standards. In some embodiments, the medical record management system may obtain the medical reporting standards from a local data store. Further, the medical reporting standards may be defined by the medical record management system or by a third party (e.g., a medical reporting standards agency). The medical record management system may periodically obtain and/or update the medical reporting standards. The medical reporting standards may include one or more reporting standards particular to the medical context, the personal injury context, the electronic medical report context, etc. Further, the medical reporting standards may identify syntax standards, writing styles, word choice, sentence and/or report structure, linguistic style, or other standards particular to medical reporting. For example, medical reporting standards may require particular word choices (e.g., particular medical terminology), may allow or reject particular text or text elements (e.g., figures of speech, questions, unclear language, etc.), may require a particular sentence structure (e.g., shorter, direct sentences), etc. Therefore, the medical record management system can obtain the medical reporting standards.

In some embodiments, the medical record management system can determine (e.g., dynamically define) frameworks for the generation of the electronic medical report based on the medical reporting standards at 404. Further, the medical record management system may verify that the frameworks satisfy the medical reporting standards. The frameworks may be frameworks for the electronic medical reports. Further, the frameworks may define an overall report organization for the electronic medical report and the frameworks may be particular to the medical context, the personal injury context, etc. The frameworks may be dynamically defined based on the medically reporting standards. For example, based on the medical reporting standards, the medical record management system can define various frameworks that satisfy the medical reporting standards and identify the framework for an electronic medical report. In some embodiments, one or more of the frameworks may be obtained from (and defined by) a third party (e.g., via a third party computing device). The medical record management system may arrange or define each of the frameworks into a narrative and/or a story plot. For example, a first framework may define a structure of a first section of an electronic medical report and a second framework may define a structure of a second section of the electronic medical report. Thus, the medical record management system can define a plurality of frameworks for the generation of electronic medical reports. Further, the frameworks may be used to build an electronic medical report based on the defined rules and the patient information. Each of the frameworks may be associated with a particular condition or a set of conditions that define when the particular framework is to be utilized. For example, the conditions may identify a particular circumstance for using particular frameworks. Further, the conditions may define the type of framework for a particular framework and may identify particular electronic medical reports or types of electronic medical reports that the framework should be utilized. In some embodiments, the medical record management system may obtain the frameworks from a third party (e.g., via a third party computing device) or may generate the frameworks. Therefore, the medical record management system can determine the frameworks based on the medical reporting standards.

In some embodiments, the medical record management system can store the frameworks based on defining or determining the frameworks at 406. The medical record management system can identify the frameworks and store the frameworks in a local or remote data store. Further, the medical record management system may identify and store the frameworks in association with one or more conditions for implementing the frameworks as discussed above. The medical record management system may utilize the one or more conditions to determine when to implement a particular framework. Therefore, the medical record management system can store the frameworks.

In some embodiments, the medical record management system can determine rules for the generation of the electronic medical report based on the medical reporting standards at 408. Further, the medical record management system may verify that the rules satisfy the medical reporting standards. The rules may define how the patient information and the frameworks are combined to generate the electronic medical report. The rules may further define how the electronic medical reports are generated from the patient information. Further, the rules may define how to transform at least a portion of the clinic notes based on the medical reporting standards. The rules may define how to transform patient information. For example, each rule may define a transformation for a particular input from the patient information to generate a particular output for the electronic medical report. Further, a rule may be for an input "left leg, right leg" the transformed output should be "both legs" and for an input "upper thigh of left leg" the transformed output should be "left leg." It will be understood that the rules may define any number of transformations for particular input. Further, the medical record management system may define rules for various language constructs. The medical record management system may determine the rules by parsing the medical reporting standards to determine the lexical choice, text style and/or choice, word choice, etc. for the electronic medical report. In some embodiments, the rules may be Extensible Stylesheet Language Transformations ("XLST") rules. In other embodiments, the rules may be any other type of rules that define lexical choice, text style and/or choice, word choice, etc. for an electronic medical report. In some embodiments, the medical record management system may obtain the rules from a third party (e.g., via a third party computing device) or may generate the rules. Therefore, the medical record management system can determine the rules based on the medical reporting standards.

In some embodiments, the medical record management system can store the rules based on defining or determining the rules at 410. The medical record management system can identify the rules and store the rules in a local or remote data store. Therefore, the medical record management system can store the rules.

5.0 Applying Frameworks and Rules

The determined frameworks and rules can be implemented in order to generate the electronic medical report. Aspects of this disclosure relate to the generation of the electronic medical report based on medical reporting standards using frameworks and rules that are particular to the medical context (e.g., the personal injury context). The medical record management system may identify and store various rules and frameworks for the generation of the electronic medical report. Further, the medical record management system may identify particular rules and a particular framework(s) for the generation of the electronic medical report. The medical record management system may parse the stored rules and frameworks to identify the relevant rules and framework(s). In order to generate the electronic medical report, the medical record management system may identify a plurality of patient information or patient information. Further, the medical record management system may utilize the patient information to identify a particular framework for the electronic medical report. The medical record management system may then identify one or more rules that are associated with the identified framework. Based on the patient information, the identified framework, and the identified one or more rules, the medical record management system can generate the electronic medical reports. Accordingly, the medical record management system may dynamically generate the electronic medical report.

Figure 5:
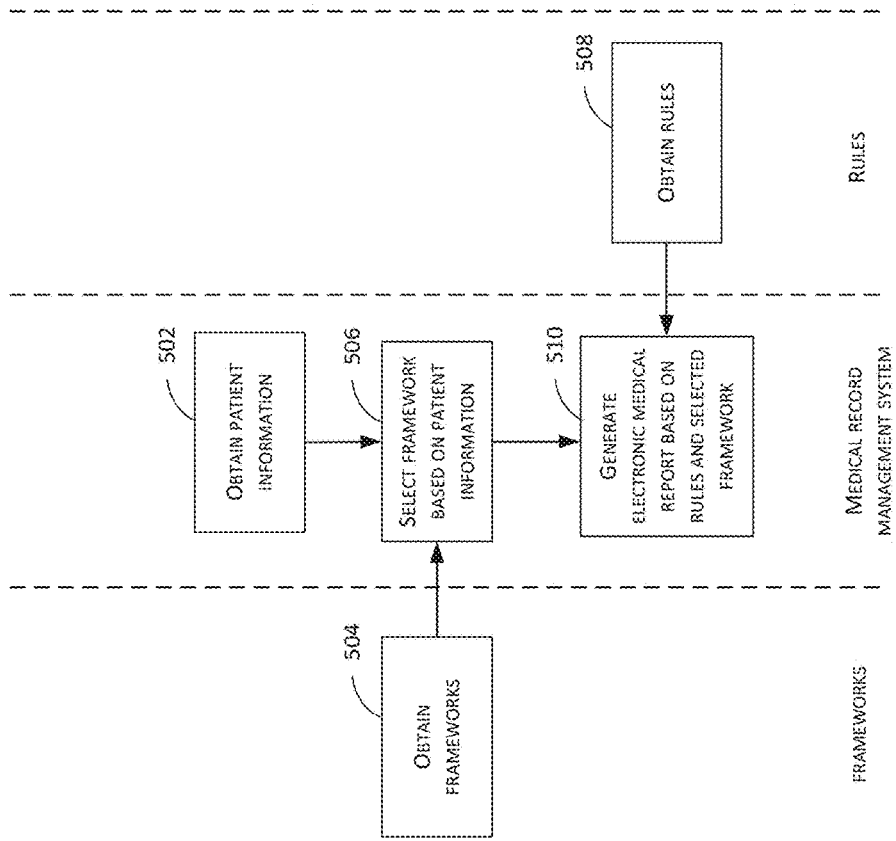
FIG. 5 illustrates an example flowchart of a method for generating an electronic medical report based on rules and a selected framework according to some embodiments herein.

FIG. 5 illustrates an example flowchart of a method 500 for generating the electronic medical report according to some embodiments herein. In some embodiments, the medical record management system can obtain patient information at 502. The medical record management system can obtain the patient information from one or more patient computing devices. Further, the medical record management system can obtain the patient information from a patient computing device and a third party computing device (e.g., a third party computing device that has received the patient information). For example, the patient computing devices can include a clinic computing device (e.g., a computing device in a medical clinic for patient intake), a user computing device (e.g., a user or client computing device that provides information about the patient), or any other computing device. The medical record management system can receive the patient information via a graphical user interface displayed on the one or more patient computing devices. Further, the medical record management system can receive a selection of particular patient information for the electronic medical report. For example, the patient information may include a selection for medical information (e.g., a selection for weight, height, gender, etc.). Further, the medical record management system can cause display of the graphical user interface for the patients. The medical record management system may utilize the selections from the patient information in order to generate the electronic medical report. Therefore, the medical record management system can obtain the patient information.

In some embodiments, the medical record management system can obtain the frameworks at 504. The medical record management system may obtain the frameworks from a plurality of previously stored frameworks. Further, the medical record management system may obtain the frameworks from a local data store or a remote data store. The medical record management system may obtain the frameworks in response to receiving a request to generate an electronic medical report and/or in response to receiving the patient information. For example, the medical record management system may continuously or periodically generate an electronic medical report with updated patient information (e.g., as updated patient information is received by the medical record management system). Therefore, the medical record management system can obtain the frameworks.

In some embodiments, the medical record management system can select a framework from the obtained frameworks based on the patient information at 506. The medical record management system can parse the obtained frameworks to identify a particular framework that is associated with the patient information. The medical record management system may compare features of the patient information to identify which templates satisfy the features and are to be utilized for the generation of the electronic medical report. For example, the patient information may identify particular features (incidents, conditions, circumstances, etc.) (e.g., a car accident and the resulting injuries to the patient) and, based on these features, the medical record management system may identify a framework for the electronic medical report. In some embodiments, the medical record management system may obtain information identifying the features or incidents separately (e.g., the medical record management system may obtain the information identifying the features from a user computing device). Further, the medical record management system can dynamically select the framework for the electronic medical report based on the identified features. In order to compare the features, the medical record management system may compare one or more values (e.g., field-values) of the features with corresponding values of the frameworks (e.g., field-values associated with a same or similar field). Therefore, the medical record management system can select the framework based on the patient information.

In some embodiments, the medical record management system can obtain the rules at 508. The medical record management system may obtain the rules from a plurality of previously stored rules. Further, the medical record management system may obtain the rules from a local data store or a remote data store. The medical record management system may obtain the rules in response to selecting a particular framework based on the patient information. Further, the medical record management system may obtain the rules based on the particular framework selected. For example, a set of rules may be associated with the particular framework and, in response to selecting the particular framework, the medical record management system may obtain the set of rules. In some embodiments, the medical record management system may obtain the rules and identify a subset of the rules that correspond to the framework based on information associated with the framework. Therefore, the medical record management system can obtain the rules.

In some embodiments, the medical record management system can generate the electronic medical report based on the obtained rules and the selected framework at 510. Based on determining and obtaining a framework and rules, the medical record management system may automatically generate a medical report that includes the obtained patient information in a format specified by the framework and the rules. Further, the medical record management system may generate multiple reports. For example, the medical record management system may generate an initial medical report, a follow-up medical report, and a discharge medical report. As discussed above, each report may be associated with (e.g., built from) a particular framework and a particular set of rules. In some embodiments, the medical record management system may generate the electronic medical report periodically or aperiodically (e.g., based on particular conditions or rules). For example, the medical record management system may generate the electronic medical report every week, every month, every two months, etc. Further, the medical record management system may generate the electronic medical report based on obtaining a request from a user. Therefore, the medical record management system can generate the electronic medical report based on the framework, rules, and the patient information.

6.0 Electronic Medical Report for User Computing Device

As discussed above, the electronic medical record module (e.g., a module of the medical record management system that generates the electronic medical report) may generate the electronic medical report periodically or aperiodically. Aspects of this disclosure further relate to the application of the rules, the framework, and the patient information in order to generate the electronic medical report. The electronic medical record module may obtain the patient information and select a framework for the electronic medical report based on the obtained patient information. Further, the electronic medical record module may implement a planning process to plan the electronic medical report based on the selected framework and the patient information. Based on the planning process, the electronic medical record module may invoke rules based on the patient information in order to identify how the patient information should be transformed to generate the electronic medical report. Using the transformed data, the electronic medical record module may then perform dynamic sentence generation to dynamically generate the sentences of the electronic medical report. The electronic medical record module may then provide the electronic medical report to a user computing system (e.g., a user computing system that requested the generation of the electronic medical report). In some embodiments, prior to providing the electronic medical report to a user computing system, the electronic medical record module may provide the electronic medical report to a third party computing device (e.g., specialist computing devices, reviewer computing devices, etc.). The third party computing device may receive the electronic medical report for review and/or approval. The third party computing device may approve, approve a modified version, and/or reject the electronic medical report. Based on identifying approval (or approval of a modified version) by the third party computing device, the electronic medical record module may route the electronic medical report to the user computing system (e.g., publish the electronic medical record module for the user computing system). In other embodiments, the electronic medical record module may provide the electronic medical report directly to the user computing system. Accordingly, the user computing system may obtain (either directly or indirectly) the electronic medical report from the electronic medical record module.

Figure 6:
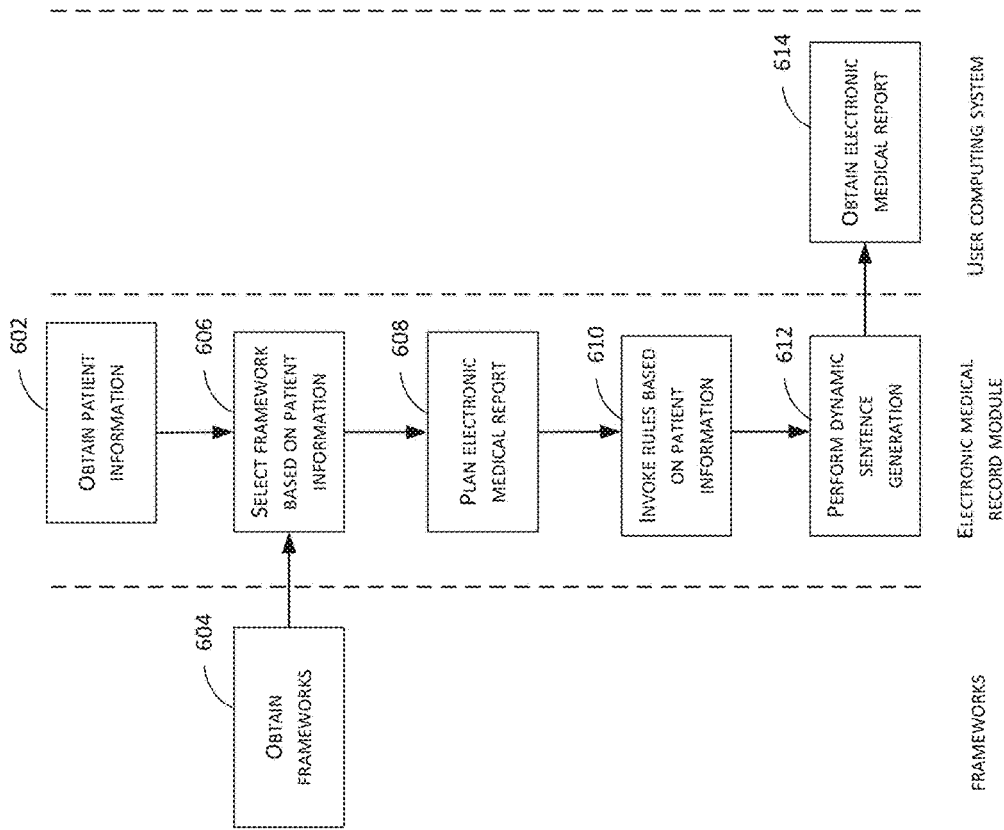
FIG. 6 illustrates an example flowchart of a method for building an electronic medical report according to some embodiments herein.

FIG. 6 illustrates an example flowchart of a method 600 for generating the electronic medical report for a user computing system according to some embodiments herein. In some embodiments, the electronic medical record module can obtain patient information at 602. As discussed above, the electronic medical record module can obtain the patient information from one or more patient computing devices. Further, the electronic medical record module may obtain clinic notes from one or more clinic computing devices. The clinic notes may include information from multiple clinics (e.g., multiple clinic notes) and may be associated with the patient. Therefore, the electronic medical record module can obtain the patient information.

In some embodiments, the electronic medical record module can obtain the frameworks at 604. The electronic medical record module may obtain the frameworks from a data store in order to determine the framework(s) that is associated with the patient information and/or the clinic notes. Therefore, the electronic medical record module can obtain the frameworks. In some embodiments, the electronic medical record module can select a framework from the obtained frameworks based on the patient information and/or the clinic notes at 606. The patient information and/or the clinic notes may be associated with one or more features, conditions, etc. For example, the patient information and/or the clinic notes may be associated with a particular feature (e.g., a type of accident) and, based on this feature, the electronic medical record module can identify the particular framework to utilize. Therefore, the electronic medical record module can select the framework based on the patient information and/or the clinic notes.

In some embodiments, the electronic medical record module plans the electronic medical report at 608. As a part of the planning process, the electronic medical record module may conduct document planning. For example, the document planning can include content planning, outlining, etc. for the electronic medical report. Based on the planning process, the electronic medical record module can prepare the electronic medical report. Further, the electronic medical record module may prepare each section of the electronic medical report and determine particular content for each section of the electronic medical report. For example, during the planning process, the electronic medical record module can plan how each subset of content from the patient information and/or the clinic notes is to be utilized for the generation of the electronic medical report.

In some embodiments, the electronic medical record module may invoke rules based on the patient information and/or the clinic notes at 610. The electronic medical record module may identify the rules that are associated with the particular framework and obtain the rules. Further, the electronic medical record module may invoke the rules to transform the clinic notes (e.g., patient information and/or clinic data). Each of the rules may correspond to a portion or subset of the patient information and/or the clinic notes and identify how to transform the patient information and/or the clinic notes into a required format for the framework (e.g., a normalized format). Further, each rule can identify one or more transformations for one or more portions of the patient information and/or the clinic notes to be included in the framework. In some embodiments, a portion of the patient information and/or the clinic notes may not be transformed and/or may not be included in the generated medical report. Based on invoking the rules, the electronic medical record module can generate transformed data (e.g., text and word-level grammatical functions) for the electronic medical report. Therefore, electronic medical record module can invoke the rules based on the patient information and/or the clinic notes.

In some embodiments, the electronic medical record module can perform the dynamic sentence generation at 612. The electronic medical record module may dynamically generate sentences for the electronic medical report from the transformed data. Based on the plan for the electronic medical report, the electronic medical record module can dynamically generate sentences from the invoked rules. Further, the electronic medical record module may dynamically generate sentences based on the medical reporting standards (e.g., a required linguistic style). For example, the dynamically generated sentences may satisfy the medical reporting standards. The electronic medical record module may generate the sentences based on the invoked rules and store the sentences. Therefore, the electronic medical record module can perform the dynamic sentence generation.

In some embodiments, the user computing device can obtain the electronic medical report from the electronic medical record module at 610. The electronic medical record module can generate the electronic medical report based on the dynamically generated sentences by aggregating the sentences into a document (e.g., the electronic medical report) and store the document. Further, the electronic medical record module can cause display of the electronic medical report at the user computing device to enable the user computing device to access the data within the electronic medical report. Further, the electronic medical record module may store the electronic medical report in a data store, the data store storing a plurality of electronic medical reports. The electronic medical record module may provide, to the user computing device, via a network, local and/or remote access to the electronic medical report based on generating (e.g., automatically generating) and storing the electronic medical report. Further, the electronic medical record module may verify that an account associated with the user computing device is authorized to access the electronic medical report prior to providing access to the user computing device. Therefore, the user computing device can obtain the electronic medical record module.

In order to generate the electronic medical report, the electronic medical record module may obtain clinic notes and perform various operations to transform the clinic notes into a format (e.g., a data format) specified by a particular framework. Based on the transformed data, the electronic medical record module may dynamically generate sentences for the electronic medical report and dynamically generate the electronic medical report. By dynamically generating the electronic medical report, the electronic medical record module can update the electronic medical report as updated clinic notes are received. Further, the electronic medical record module can generate an electronic medical report that compiles or aggregates a plurality of clinic notes.

Figure 7A:
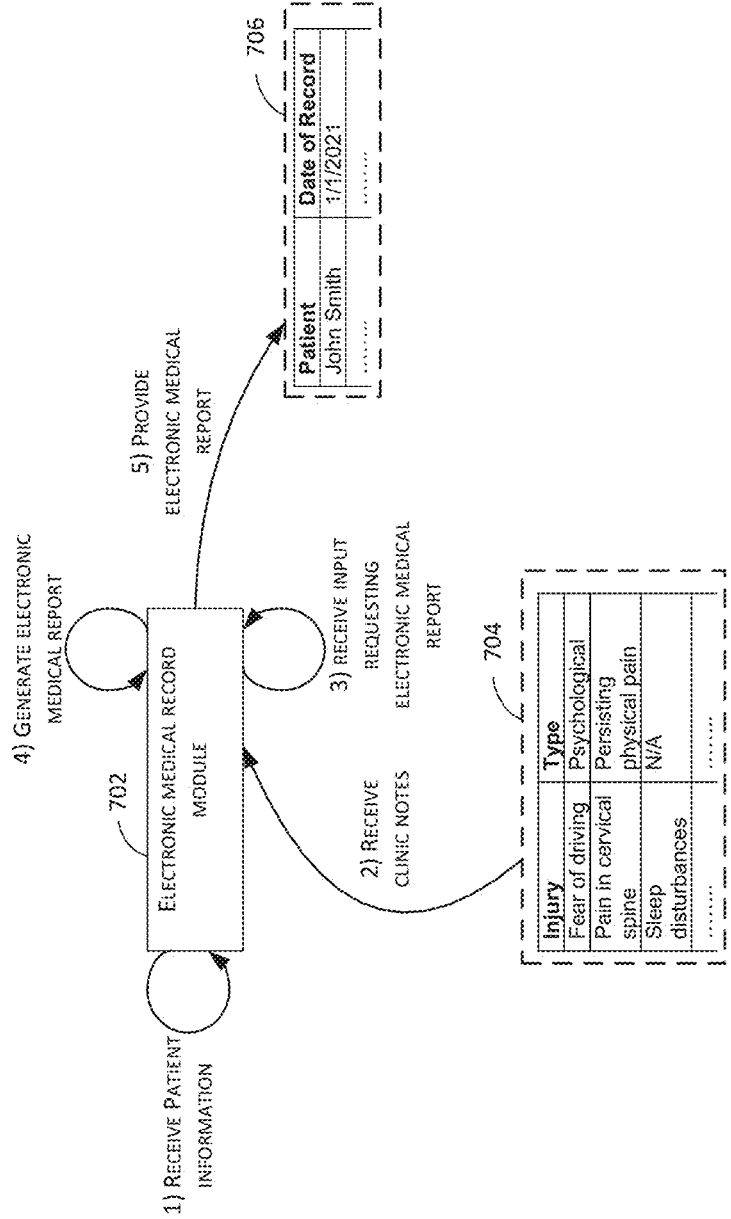
FIG. 7A depicts a schematic diagram of a system including an electronic medical record module according to some embodiments herein.

FIG. 7A depicts a schematic diagram of a system 700A including an electronic medical record module 702 according to some embodiments herein. The electronic medical record module 702 may be in communication with one or more patient computing devices, one or more user computing devices, one or more clinic computing devices, or any other computing devices. The electronic medical record module 702 may dynamically generate an electronic medical report based on received information associated with a patient.

At (1), the electronic medical record module 702 can receive the patient information. The patient information may identify information associated with the patient. Further, the electronic medical record module 702 may receive the patient information from a patient computing device, a user computing device, etc.

At (2), the electronic medical record module 702 can receive clinic notes 704. The clinic notes 704 may include information about or associated with the patient and/or information about or associated with the medical treatment or diagnosis of the patient. In the example of FIG. 7A, the clinic notes 704 include various fields and various field-values. For example, the clinic notes 704 include field "Injury" and field-values "Fear of driving," "Pain in cervical spine," and "Sleep disturbances" and field "Type" and field-values "Psychological," "Persisting physical pain," "N/A." It will be understood that the clinic notes 704 may include more, less, or different notes. Further, it will be understood that the clinic notes 704 in any format.

At (3), the electronic medical record module 702 can receive input requesting an electronic medical report. The electronic medical record module 702 may receive the input from a user computing device. Further, the request may include a patient identifier. Based on the patient identifier, the electronic medical record module 702 may identify an electronic medical report for generation.

At (4), the electronic medical record module 702 can generate the electronic medical report. As discussed above, the electronic medical record module 702 may dynamically generate the electronic medical report based on the clinic notes and the patient information.

Figure 7B:
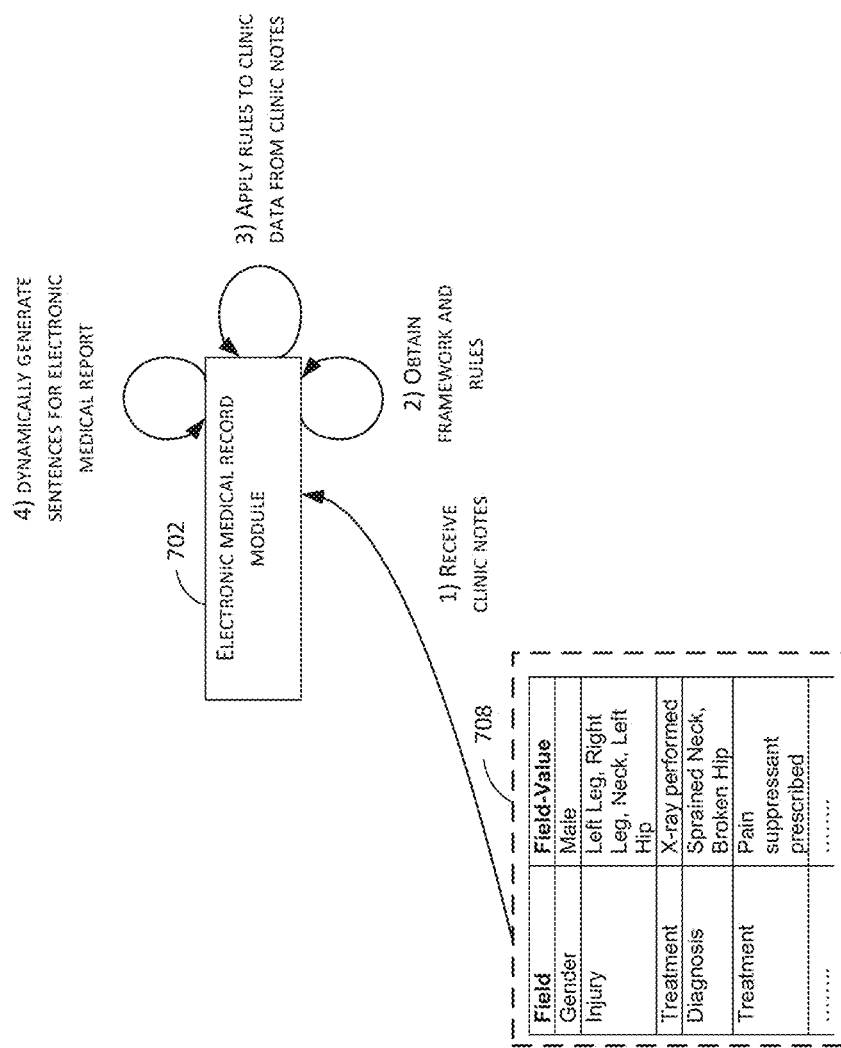
FIG. 7B depicts a schematic diagram of a system including an electronic medical record module according to some embodiments herein.

At (5), the electronic medical record module 702 can provide the electronic medical report. The electronic medical record module 702 may route the electronic medical report to a user computing device. Further, the electronic medical record module 702 may cause display of the electronic medical report at the user computing device. In the example of FIG. 7B, the electronic medical report 706 includes various fields and various field-values. For example, the electronic medical report 706 includes a field "Patient" and a field-value "John Smith" and a field "Date of Record" and a field-value "1/1/2021." It will be understood the electronic medical report may include more, less, or different information.

FIG. 7B depicts a schematic diagram of a system 700B including an electronic medical record module 702 according to some embodiments herein. The electronic medical record module 702 may be in communication with one or more patient computing devices, one or more user computing devices, one or more clinic computing devices, or any other computing devices. The electronic medical record module 702 may dynamically generate an electronic medical report based on received information associated with a patient.

At (1), the electronic medical record module 702 can receive the clinic notes 708. The clinic notes 708 may include information about or associated with the patient and/or information about or associated with the medical treatment of the patient. The clinic notes 708 may be collected and/or provided by one or more clinic computing devices. In some embodiments, the clinic notes 708 may include multiple sets of clinic notes. The electronic medical record module 702 may receive the clinic notes 708 separately or as a compiled set of clinic notes 708. For example, the clinic notes 708 may include clinic notes from multiple clinics (e.g., multiple clinic computing devices). In the example of FIG. 7B, the clinic notes 708 include various fields and various field-values. For example, the clinic notes 708 include field "Gender" and field-value "Male," field "Injury" and field-value "Left Leg, Right Leg, Neck, Left Hip," field "Treatment" and field-value "X-ray performed," field "Diagnosis" and field-value "Sprained Neck, Broken Hip," and field "Treatment" and field-value "Pain Suppressant Prescribed." It will be understood that the clinic notes 708 may include more, less, or different notes. Further, it will be understood that the clinic notes 708 in any format. The electronic medical record module 702 may parse the clinic notes 708 and store the clinic notes 708 or a particular portion of the clinic notes 708 in a database. For example, the electronic medical record module 702 may store the clinic notes 708 as a file (e.g., an extensible markup language file). The clinic notes 708 may include patient information (e.g., information about the patient such as height, weight, etc.) and clinic data (e.g., information about the medical treatment of the patient such as operations performed or injures documented).

At (2), the electronic medical record module 702 can obtain the framework and the rules. For example, the electronic medical record module can obtain the framework and the rules that are associated with a particular patient (e.g., that are associated with particular conditions that the patient satisfies). Further, the electronic medical record module may select a particular framework and associated rules based on parsing data associated with the patient. Each framework may be linked or associated with a specific type of electronic medical report. Each framework may be associated with particular information and may be associated with a particular set of rules in order to transform clinic notes to obtain the information. Further, the rules may be dynamically obtained and updated by the electronic medical record module 702. For example, the rules may be updated periodically as the electronic medical record module 702 loads the rules.

At (3), the electronic medical record module 702 can apply the rules to the clinic notes. In order to apply the rules to the clinic notes, the electronic medical record module 702 may parse the rules to identify how to transform the clinic notes. For example, a rule may indicate that if the clinic notes identify the patient gender as male, the clinic notes can be transformed to identify the term "Mr." should be used throughout the electronic medical report. Further, the rule may indicate that the clinic notes can be transformed to generate particular pronouns (e.g., his and he) that should be used throughout the electronic medical report. Therefore, the electronic medical record module 702 may parse the clinic notes and identify that the clinic notes indicate the patient gender is identified as male. Further, the rule will be applied to transform the clinic notes and implement the transformed data throughout the electronic medical report based on the framework. In another example, a rule may indicate that if the clinic notes indicate that the left leg and the right leg are injured, the rule will transform the clinic notes to identify that both legs are injured. Further, the rule may indicate that if the clinic notes indicate that the left leg and the left arm are injured, the rule will transform the clinic notes to indicate that the left leg and the left arm are injured. In another example, a rule may indicate that if the clinic notes indicate that an x-Ray was performed, the rule will cause the dynamic generation of a sentence identifying that the x-Ray was performed.

At (4), the electronic medical record module 702 can dynamically generate the sentences for the electronic medical report. For example, the electronic medical record module 702 may dynamically generate a sentence with the transformed data (e.g., the sentence may be "Mr. Smith injured both legs and an X-ray was performed that indicated a sprained neck and a broken hip. In response, a pain suppressant was prescribed"). The electronic medical record module 702 may dynamically generate multiple sentences for the electronic medical report. Further based on this dynamic generation, the electronic medical record module 702 can dynamically compile the dynamically generated sentences to form the electronic medical report based on the identified framework and rules.

7.0 Example Electronic Medical Report

FIG. 8 depicts an example user interface 800 for providing access to an electronic medical report for review by a user. The example user interface 800 is illustrative of an interface that the electronic medical record module of the medical record management system generates and presents to a user to provide the user access to an electronic medical report. In the example of FIG. 8, the user interface 800 includes a report corresponding to a particular patient for which the user has requested the report. Thus, in the illustrated example, the report is referred to as an "electronic medical report" and the user interface 800 enables the user to interact with and/or parse data from the electronic medical report. As will be described in more detail below, the medical record management system may present the electronic medical report to a user (e.g., via a user computing device) so that the user can review and parse the electronic medical report. It will be understood that FIG. 8 is illustrative only, and the medical record management system, via the user interface 800, may offer any type of medical report for browsing by a user.

Via the user interface 800, the medical record management system can provide the electronic medical report. In order to generate and provide the electronic medical report, the medical record management system can receive a designation of a patient (e.g., information identifying a patient such as a patient number). The medical record management system may also receive additional patient information. Further, as discussed above, the medical record management system can receive clinic notes. For example, the medical record management system may receive clinic notes from a primary care physician (e.g., a computing device or system associated with a primary care physician), a physical therapist (e.g., a computing device or system associated with a physical therapist, a dentist (e.g., a computing device or system associated with a dentist), etc. Based on the obtained information, the medical record management system can generate the electronic medical report for display to a user.

Based on the patient that has been selected for the electronic medical report and the clinic notes, the user interface 800 may include a designation of medical analysis associated with the patient. For example, the user interface 800 includes a summarization of the medical analysis that was conducted by a third party (e.g., a medical professional). The user interface 800 may include additional settings that enable a user to modify the data included in the electronic medical report. For example, a user may customize and/or filter the electronic medical report in order to cause display of a filtered portion of the electronic medical via the user interface 800.

In some embodiments, the user interface 800 identifies multiple electronic medical reports generated by the medical record management system. For example, the user interface 800 may identify multiple electronic medical reports associated with the same patient. Further, the user interface 800 may identify electronic medical reports associated with multiple patients. For example, the user interface 800 may identify a first electronic medical report associated with a first patient and a second electronic medical report associated with a second patient. Via the user interface 800, the user can select particular electronic medical reports and/or particular patients in order to identify a particular electronic medical report for display. For example, the user may select a particular electronic medical report and cause display of the particular electronic medical report. Further, the medical record management system may make particular electronic medical reports available to some users and not available to other users. Prior to providing a user access to a particular electronic medical report, the medical record management system may verify that a particular user is authorized to view the electronic medical report.

Returning to FIG. 8, the user interface 800 may include a patient or electronic medical report identifier. The identifier may identify a particular patient and/or a particular electronic medical report associated with a particular patient and provide information about the particular patient and/or the electronic medical report. A user may toggle the identifier in order to select a particular patient or a particular electronic medical report. For example, the user may interact with the identifier to select a particular electronic medical report for review. The identifier may correspond to any numerical, alphabetical, alphanumerical, or symbolical string. For example, the identifier may include a patient number, a patient identifier, etc.

The user interface 800 may further include a first interface 802A and a second interface 802B. The user interface 800 may further include more, less, or different interfaces. The first interface 802A may be an initial visit interface and the second interface 802B may be a follow-up visit interface. For example, the initial visit interface may identify an electronic medical report associated with an initial visit and the follow-up visit interface may identify an electronic medical report associated with a subsequent, related, follow-up visit. In some embodiments, the user interface 800 may include interfaces for unrelated visits. A particular patient, as identified by the identifier, may correspond to a plurality of visits. The user interface 800 may include separate, distinct interfaces for each of the plurality of visits corresponding to the user.

In some embodiments, the user interface 800 may further include a settings interface. The settings interface may identify one or more user configurable settings for which the user can modify in order to modify how the electronic medical report is generated and/or provided to the user. For example, the settings may enable a user to specify a schedule for verifying whether updates are available for the electronic medical report. Further, the settings may enable a user to specify a particular format for the electronic medical report.

Each of the first interface 802A and the second interface 802B may include multiple interfaces. For example, the first interface 802A may include a first interface 804, a second interface 806, a third interface 808, a fourth interface 810, and a fifth interface 812. It will be understood that the first interface 802A may include more, less, or different interfaces. Each of the first interface 804, the second interface 806, the third interface 808, the fourth interface 810, and the fifth interface 812 may identify or define a portion of the electronic medical report. In some embodiments, the first interface 802A may include a single interface that identifies or defines the electronic medical report. Each of the first interface 804, the second interface 806, the third interface 808, the fourth interface 810, and the fifth interface 812 may include a portion of the information generated by the medical record management system for generation of the electronic medical report.

The first interface 804 may identify a clinic (e.g., an office of a medical professional) that is associated with the electronic medical report. For example, a computing device associated with the clinic may provide the clinic notes for generation of the electronic medical report. The first interface 804 may include identifying information about the clinic. For example, the first interface 804 may include a title, an address, an e-mail address, a leading medical professional, information associated with one or more medical professionals, a phone number, or any other information about or associated with the clinic. In the example of FIG. 8, the first interface 804 identifies the clinic information as "Acme Physicians Associates Acme Group 183 Main Street, Acme." It will be understood that the first interface 804 may include more, less, or different information.

The second interface 806 may identify information associated with a visit to a clinic (e.g., information identifying the particular visit to the clinic). The second interface 806 may identify a particular visit that is associated with the electronic medical report. Further, a computing device associated with the clinic may provide the clinic notes and identify the particular visit that the clinic notes correspond. The second interface 806 may include identifying information about the visit. For example, the second interface 806 may include a type of visit, a type of test run, a data of injury, a date of the visit, or any other information associated with the visit. In the example of FIG. 8, the second interface 806 identifies the visit information as "Initial Visit Re: Patient 1 (Rn) Sample Date of Injury: Feb. 1, 8018 Date of Visit Mar. 1, 8081." It will be understood that the second interface 806 may include more, less, or different information.

The third interface 808 may identify information associated with a patient (e.g., information identifying the particular patient for the electronic medical report). The third interface 808 may identify a particular patient who corresponds to the particular electronic medical report. Further, a computing device associated with the clinic and/or a computing device associated with the user may provide the information associated with the patient. The third interface 808 may include identifying information about the patient. For example, the third interface 808 may include a name, an age, a gender, a dominant hand, a type of accident, a data of accident, or any other information associated with the patient. In the example of FIG. 8, the third interface 808 identifies the visit information as "Mr. Sample is an 81-year-old right-handed male who was involved in an auto accident on Feb. 1, 8018. The history, obtained from the patient is as follows:" It will be understood that the third interface 808 may include more, less, or different information.

The fourth interface 810 may identify information associated with the accident (e.g., information identifying the accident and/or the reason for the visit to the clinic). The fourth interface 810 may identify a particular accident with the electronic medical report. Further, a computing device associated with the clinic may provide the notes about the accident and the treatment for the patient. The fourth interface 810 may identify information associated with the accident and/or information associated with the subsequent visit to the clinic. For example, the fourth interface 810 may include a type of accident, what happened during the accident, treatment of the patient, symptoms of the patient, or any other information associated with the accident. In the example of FIG. 8, the fourth interface 810 identifies the accident information as "Mr. Sample was a seat-belted driver in a moving car which was hit in the front by another car. Upon impact his body moved forward and backward. He injured his cervical spine. Persisting pain in the injured area, post-traumatic anxiety, a fear of driving, sleep disturbance and problems concentrating caused Mr. Sample to visit the clinic seeking medical assistance. This symptom developed right after the accident." It will be understood that the fourth interface 810 may include more, less, or different information.

The fifth interface 812 may identify miscellaneous information associated with the electronic medical report. The fifth interface 812 may identify information from the clinic notes that was not included in the first interface 804, the second interface 806, the third interface 808, or the fourth interface. The fifth interface 812 may include identifying information about the visit, the patient, the accident, the clinic, etc. In the example of FIG. 8, the fifth interface 812 identifies the miscellaneous information as "In spite of his injury, Mr. Sample continues his daily activities under duress." It will be understood that the fifth interface 812 may include more, less, or different information.

8.0 User Interface for Receiving Patient Information

FIG. 9 depicts an example user interface 900 for providing access to an intake form (e.g., an electronic intake form) for review by a clinic computing system. The example user interface 900 is illustrative of an interface that the electronic medical record module of the medical record management system generates and presents to a clinic computing system to enable the clinic computing to provide clinic notes. In some embodiments, the electronic medical record module can cause display of the user interface 900 via a display of the clinic computing system. In the example of FIG. 9, the user interface 900 includes example clinic notes for a patient. As will be described in more detail below, the medical record management system may present the intake form to a medical professional (e.g., a doctor via the clinic computing system) so that the medical professional can provide the clinic notes for a patient via the intake form. It will be understood that FIG. 9 is illustrative only, and the medical record management system, via the user interface 900, may offer any type of intake form.

Via the user interface 900, the medical record management system can provide the intake form. In order to determine how to provide the intake form, the medical record management system may identify a particular patient (e.g., the medical record management may obtain a designation of the particular patient via a patient number of patient identifier). Based on the identified patient, the medical record management system may build a particular intake form for the patient. For example, the intake form may include one or more questions particular to the particular patient. Further, a patient in a vehicular accident may have an intake form that includes a question about whether the patient was seat-belted and a patient who is a victim of a bodily assault may not have an intake form that includes the particular question. Therefore, the medical record management system can dynamically build the intake form. In some embodiments, the medical record management system may select the intake form from a plurality of intake forms based on the patient information.

In some embodiments, the user interface 900 may identify the particular patient. The clinic computing system may be required to provide identifying information of the patient (e.g., a patient identifier) in order to verify that the clinic computing system is authorized to access the intake form for the patient. For example, the user interface 900 may identify intake forms generated by the medical record management system. For example, the user interface 900 may identify multiple intake forms associated with the same patient. Further, the user interface 800 may identify intake forms associated with multiple patients.

Returning to FIG. 9, the user interface 900 may further include a first interface 902A, a second interface 902B, a third interface 902C, a fourth interface 902D, a fifth interface 902E, and a sixth interface 902F. The user interface 900 may further include more, less, or different interfaces.

The first interface 902A may be a general information interface. The first interface 902A may enable the clinic computing system to provide general information associated with the patient. For example, the first interface 902A may include one or more fillable and/or interactive fields in order to provide general information associated with the patient. The general information of the patient may include an address of the patient, a date of birth of the patient, a phone number of the patient, or any other general information associated with the patient. It will be understood that the first interface 902A may include more, less, or different information.

The second interface 902B may be an accident information interface. The second interface 902B may enable the clinic computing system to provide accident information associated with the patient. For example, the second interface 902B may include one or more fillable and/or interactive fields in order to provide accident information associated with the patient. The second interface 902B may further enable accident information associated with a personal injury of the patient to be provided. The accident information of the patient may include a type of accident, a date of the accident, pictures of the accident, or any other accident information associated with the patient. It will be understood that the second interface 902B may include more, less, or different information.

The third interface 902C may be a medical history interface. The third interface 902C may enable the clinic computing system to provide a medical history associated with the patient. For example, the third interface 902C may include one or more fillable and/or interactive fields in order to provide the medical history associated with the patient. The third interface 902C may further enable the provision of medical history related to the personal injury of the patient. For example, if the patient injured a right leg as a result of the accident, the third interface 902C may include one or more fields specific to the right leg. The medical history of the patient may include a history of injuries, a history of medical treatment, a history of accidents, or any other medical history associated with the patient. It will be understood that the third interface 902C may include more, less, or different information.

The fourth interface 902D may be an injuries interface. The fourth interface 902D may enable the clinic computing system to provide injury information associated with the patient. For example, the fourth interface 902D may include one or more fillable and/or interactive fields in order to provide the injury information associated with the patient. The injury information of the patient may include a type of injury, an identification of the location of the injury, a date of the injury, a cause of the injury, a result of the injury, or any other injury information. It will be understood that the fourth interface 902D may include more, less, or different information.

The fifth interface 902E may be a general exam interface. The fifth interface 902E may enable the clinic computing system to provide general exam information by a medical professional associated with the patient. For example, the fifth interface 902E may include one or more fillable and/or interactive fields in order to provide general exam information associated with the patient. The general exam information of the patient may include a date of the general examination, results of the general examination, or any other general exam information associated with the patient. It will be understood that the fifth interface 902E may include more, less, or different information.

The sixth interface 902F may be a physical exam interface. The sixth interface 902F may enable the clinic computing system to provide physical exam information by a medical professional associated with the patient. For example, the sixth interface 902F may include one or more fillable and/or interactive fields in order to provide physical exam information associated with the patient. In some embodiments, the medical professional providing the general exam information and the medical professional providing the physical exam information may be different medical professionals. The physical exam information of the patient may include a date of the physical examination, results of the physical examination, or any other physical exam information associated with the patient. It will be understood that the sixth interface 902F may include more, less, or different information.

Each of the first interface 902A, the second interface 902B, the third interface 902C, the fourth interface 902D, the fifth interface 902E, and the sixth interface 902F may include multiple interfaces. For example, the second interface 902B may include a first interface 904 and a second interface 908. It will be understood that the second interface 902B may include more, less, or different interfaces. Each of the first interface 904 and a second interface 908 may identify or define a portion of the intake form for obtaining the accident information. In some embodiments, the second interface 902B may include a single interface that identifies or defines the intake form for obtaining the accident information.

The first interface 904 may identify an intake form for receiving accident information. The accident information may be associated with an accident related to a personal injury of a patient. For example, a patient may experience a personal injury and seek medical assistance from a medical clinic and a clinic computing system of the medical clinic may provide the accident information to the medical record management system via the first interface 904. The first interface 904 may include prompts (e.g., fillable, modifiable, interactive, etc. fields) to receive the accident information from the clinic computing system. For example, the first interface 904 may include a date of the accident, a type of the accident, a severity of the accident, or any other information about or associated with the accident. In some embodiments, all or a portion of the first interface 904 may be displayed based on a prior response by the clinic computing system. For example, if the clinic computing system indicates that the accident was a vehicular accident, a first plurality of fields may be displayed in the first interface 904 and, if the clinic computing system indicates that the accident was a bodily assault, a second plurality of fields may be displayed in the first interface 904. In the example of FIG. 9, the first interface 904 identifies the accident information as including a "type of accident" field with an "Auto" selected field value from "MTA," "Motorcycle," "Scooter," "Bicycle," or "Other" possible field values, a "car accident" identifier, a "were you" field with "Driver" or "Passenger" possible field values, an "accident happened" field with "Moving," "Stopped," or "Parked" possible field values, a "you were in a" field with "Car," "SUV," "Van," "Pick-up Truck," "Taxi," or "Bus" possible field values, an "it was" field with "N/A," "Your own," "Parent's," or "Company Car" possible field values, a "seat-belted" field with "Yes" or "No" possible field values, a "vehicle towed" field with "Yes" or "No" possible field values, and an "airbags deployed" field with "Yes" or "No" possible field values. It will be understood that the first interface 904 may include more, less, or different information.

The second interface 908 may identify an intake form for receiving post-accident information. The post-accident information may be associated with an accident related to a personal injury of a patient and may capture information after the accident. For example, a patient may experience a personal injury and seek medical assistance from a medical clinic and a clinic computing system of the medical clinic may provide the post-accident information to the medical record management system via the second interface 908. The second interface 908 may include prompts (e.g., fillable, modifiable, interactive, etc. fields) to receive the post-accident information from the clinic computing system. For example, the second interface 908 may include information about the patient after the accident to identify how the accident affected the patient. In the example of FIG. 9, the second interface 908 identifies the post-accident information as including an "at the scene there was" field with "Police," "Fire Department," or "Ambulance" possible field values, a "complaints" identifier, an "able to perform work" field with "No," "Yes," "Do Not Work," or "Lost Job" possible field values, an "other limitations" field with "Hobbies," "Sports," or "Domestic Duties" possible field values, a "paid household assistance" field with "Yes" or "No" possible field values, and a "relationship issues" field with "Yes" or "No" possible field values. It will be understood that the second interface 908 may include more, less, or different information.

9.0 User Interface for Receiving Injury Data

FIG. 10 depicts an example user interface 1000 for providing access to an intake form (e.g., an electronic intake form) for review and submission by a clinic computing system. The example user interface 1000 is illustrative of an interface that the electronic medical record module of the medical record management system generates and presents to a clinic computing system to enable the clinic computing to provide clinic notes. The example user interface 900, as discussed above, and the example user interface 1000 may be examples of user interfaces provided to a medical professional, via a clinic computing system, for receiving clinic notes. It will be understood that the user interface 900 and the user interface 1000 are illustrative only, and the medical record management system may offer any type of user interface to obtain the clinic notes.

As discussed above, via the user interface 1000, the medical record management system can provide the intake form based on an identified patient. Further, the medical record management system can dynamically build the intake form. In some embodiments, the clinic computing system may be required to provide identifying information of the patient (e.g., a patient identifier) in order to verify that the clinic computing system is authorized to access the intake form for the patient.

Returning to FIG. 10, the user interface 1000 may further include a first interface 1002A, a second interface 1002B, a third interface 1002C, a fourth interface 1002D, a fifth interface 1002E, and a sixth interface 1002F. The user interface 1000 may further include more, less, or different interfaces. As discussed above, the first interface 1002A may be a general information interface, the second interface 1002B may be an accident information interface, the third interface 1002C may be a medical history interface, the fourth interface 1002D may be an injuries interface, the fifth interface 1002E may be a general exam interface, and the sixth interface 1002F may be a physical exam interface.

Each of the first interface 1002A, the second interface 1002B, the third interface 1002C, the fourth interface 1002D, the fifth interface 1002E, and the sixth interface 1002F may include multiple interfaces. For example, the fourth interface 1002D may include an interface 1004. It will be understood that the fourth interface 1002D may include more, less, or different interfaces. The interface 1004 may identify or define a portion of the intake form for obtaining the injuries information.

The interface 1004 may identify an intake form for receiving the injuries information. The injuries information may include injury information associated with a particular accident (e.g., the accident identified by the accident information and post-accident information of FIG. 9). The injuries information may be associated with one or more injuries and one or more accidents. For example, the injuries information may be associated with a first personal injury and a second personal injury caused by a first accident and a third personal injury caused by a second accident. The interface 1004 may include prompts (e.g., fillable, modifiable, interactive, etc. fields) to receive the injuries information from the clinic computing system. For example, the interface 1004 may include a date of the injury, a type of the injury, a severity of the injury, or any other injuries information. In the example of FIG. 10, the interface 1004 identifies the following fields "Area," "Pain Level," "Sprain/Strain," "Traumatic Injuries," "Contusion/Superficial Injury," "Bruising," and "Scars." Each field may be associated with a particular field value to identify the injury. For example, the injuries information includes an injury to the "Occipital" area with a "Mild" pain level, a "N/A" sprain/strain, a "N/A" traumatic injuries, a "Healed" contusion/superficial injury, a non-selected field for bruising, and a non-selected field for scars, an injury to the "Cervical Spine" area with a "Moderate" pain level, an "Improved" sprain/strain, a "N/A" traumatic injuries, a "N/A" contusion/superficial injury, a selected field for bruising, and a non-selected field for scars, an injury to the "Thoracic Spine" area with a "High" pain level, a "Worsened" sprain/strain, a "The Same" traumatic injuries, an "N/A" contusion/superficial injury, a non-selected field for bruising, and a non-selected field for scars, an injury to the "Trapezius Left" area with a "Mild" pain level, a "New" sprain/strain, a "N/A" traumatic injuries, a "N/A" contusion/superficial injury, a non-selected field for bruising, and a non-selected field for scars, and an injury to the "Trapezius Right" area with an "Unknown" pain level, an "Unknown" sprain/strain, an "Unknown" traumatic injuries, an "Unknown" contusion/superficial injury, a non-selected field for bruising, and a non-selected field for scars. It will be understood that the interface 1004 may include more, less, or different information.

10.0 Computing System

Figure 11:
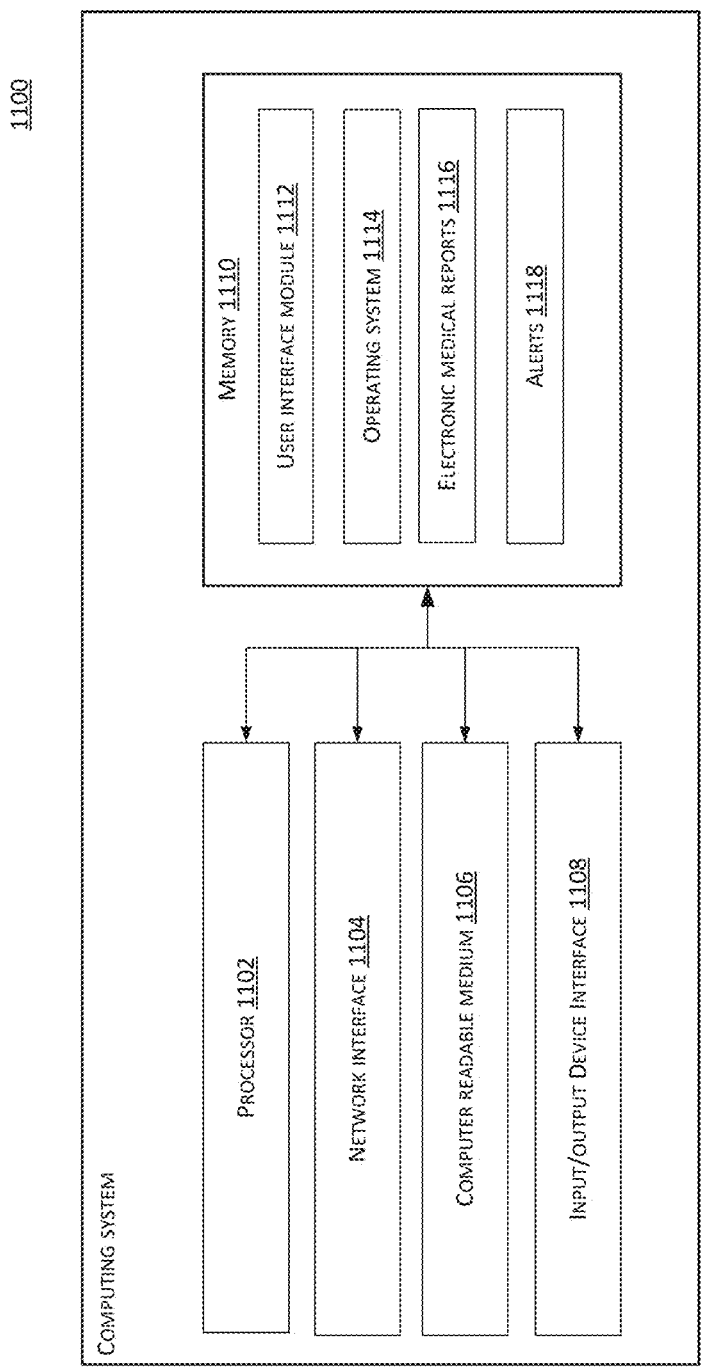
FIG. 11 illustrates an example computing system for performing various operations according to some embodiments herein.

FIG. 11 illustrates an example computing system 1100 that executes the processes and implement the features described above. In some embodiments, the computing system 1100 includes: one or more processors (e.g., processing units) 1102, such as physical central processing units ("CPUs"); one or more network interfaces 1104, such as a network interface cards ("NICs"); one or more computer readable medium drives 1106, such as a high density disk ("HDDs"), solid state drives ("SDDs"), flash drives, and/or other persistent non-transitory computer-readable media; an input/output device interface 1108, such as an IO interface in communication with one or more microphones; and one or more computer-readable memories 1110, such as random access memory ("RAM") and/or other volatile non-transitory computer-readable media.

The network interface 1104 can provide connectivity to one or more networks or computing systems. The one or more processors 1102 can receive information and instructions from other computing systems or services via the network interface 1104. The network interface 1104 can also store data directly to the computer-readable memory 1110. The one or more processors 1102 can communicate to and from the computer-readable memory 1110, execute instructions and process data in the computer-readable memory 1110, etc.

The computer-readable memory 1110 may include computer program instructions that the one or more processors 1102 execute in order to implement one or more embodiments. The computer-readable memory 1110 can store a user interface module 1112 for utilizing and enabling interactions with a user via the input/output device interface 1108. The computer-readable memory 1110 can store an operating system 1114 that provides computer program instructions for use by the one or more processors 1102 in the general administration and operation of the computing system 1100. The computer-readable memory 1110 can further include computer program instructions and other information for implementing aspects of the present disclosure. For example, in one embodiment, the computer-readable memory 1110 includes electronic medical reports 1116. As another example, the computer-readable memory 1110 may include alerts 1118.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware, or as a combination of electronic hardware and executable software. To clearly illustrate this interchangeability, various illustrative components, blocks, modules, and steps have been described above generally in terms of their functionality. Whether such functionality is implemented as hardware, or as software that runs on hardware, depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry that processes computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. A computer-implemented method for generation of an electronic medical report satisfying medical reporting standards from clinic notes with different data formats, the computer-implemented method comprising:

obtaining patient information, the patient information comprising one or more key-value pairs, wherein the one or more key-value pairs identify one or more characteristics of a patient;

obtaining clinic notes from a clinic computing system via an application programming interface, wherein the clinic notes are associated with the patient, wherein the clinic notes identify one or more of an incident, a medical treatment, or a medical diagnosis associated with a personal injury of the patient, wherein the clinic notes comprise first clinic notes and second clinic notes, wherein the first clinic notes and the second clinic notes have different data formats and comprise a plurality of clinic information, wherein a first data format of the first clinic notes and a second data format of the second clinic notes is based on one or more hardware components or one or more software components of the clinic computing system;

obtaining, from a user computing device, a request to generate the electronic medical report, the electronic medical report corresponding to the personal injury of the patient, wherein the request to generate the electronic medical report identifies a context of the electronic medical report as a personal injury context;

automatically generating, in real time, the electronic medical report based on obtaining the request to generate the electronic medical report, wherein generating the electronic medical report comprises:

obtaining one or more medical reporting standards based on the context of the electronic medical report, wherein the one or more medical reporting standards identify one or more standards for generation of the electronic medical report, dynamically defining one or more report structures for generation of the electronic medical report based on the one or more medical reporting standards, wherein the one or more report structures are arranged to define a narrative for the electronic medical report, determining one or more rules from a plurality of rules for the generation of the electronic medical report based on the one or more medical reporting standards, wherein the one or more rules define how to transform at least a portion of the clinic notes based on the one or more medical reporting standards, dynamically mapping the one or more rules to the one or more report structures to generate an electronic medical report structure, filtering the one or more key-value pairs of the patient information to identify a subset of the one or more characteristics of the patient, transforming the at least a portion of the clinic notes based on the one or more rules, dynamically generating one or more sentences based at least in part on the filtered one or more key-value pairs and the transformed portion of the clinic notes, and dynamically building the electronic medical report by incorporating the one or more dynamically generated sentences in to the electronic medical report structure, wherein the electronic medical report satisfies the one or more medical reporting standards, wherein the electronic medical report has a standardized data format, wherein the first clinic notes, the second clinic notes, and the electronic medical report have different data formats;

storing the electronic medical report in a data store, the data store storing a plurality of electronic medical reports; and providing, to the user computing device via a network, remote or local access to the electronic medical report based on automatically generating and storing the electronic medical report and verifying that an account associated with the user computing device is authorized to access the electronic medical report.

2. The computer-implemented method of claim 1, wherein obtaining the request to generate the electronic medical report is based on obtaining the clinic notes from the clinic computing system.

3. The computer-implemented method of claim 1, wherein the clinic notes further comprises a plurality of clinic notes, the plurality of clinic notes comprising the first clinic notes and the second clinic notes, wherein obtaining the clinic notes comprises obtaining the plurality of clinic notes from a plurality of clinic computing systems, wherein obtaining the plurality of clinic notes from the plurality of clinic computing systems comprises:

obtaining the first clinic notes from a first clinic computing system of the plurality of clinic computing systems; and obtaining the second clinic notes from a second clinic computing system of the plurality of clinic computing systems, wherein the first clinic computing system and the second clinic computing system are associated with different clinics, wherein the first clinic computing system and the second clinic computing system are associated with one or more of different hardware components or different software components.

4. The computer-implemented method of claim 1, wherein dynamically building the electronic medical report comprises combining the first clinic notes and the second clinic notes using the standardized data format.

5. The computer-implemented method of claim 1, wherein the one or more medical reporting standards further identify one or more of a syntax standard, a writing style, a word choice, a sentence structure, a report structure, or a linguistic style, wherein the one or more medical reporting standards cause at least one of:

requirement of particular medical terminology, allowance or rejection of at least one of figures of speech, questions, or unclear language, or requirement of shorter, direct sentences.

6. The computer-implemented method of claim 1, wherein generating the electronic medical report further comprises parsing the medical reporting standards to determine the one or more rules, wherein the one or more rules further define at least one of a lexical choice, a text style choice, or a word choice for the electronic medical report.

7. A medical record management system for generation of an electronic medical report satisfying medical reporting standards from clinic notes with different data formats, the medical record management system comprising:

a data store configured to store one or more electronic medical reports; and an electronic medical record module in communication with the data store, wherein the electronic medical record module is configured to at least:

obtain patient information, the patient information comprising one or more key-value pairs, wherein the one or more key-value pairs identify one or more characteristics of a patient;

obtain clinic notes from a clinic computing system via an application programming interface, wherein the clinic notes are associated with the patient, wherein the clinic notes identify one or more of an incident, a medical treatment, or a medical diagnosis associated with a personal injury of the patient, wherein the clinic notes comprise first clinic notes and second clinic notes, wherein the first clinic notes and the second clinic notes have different data formats and comprise a plurality of clinic information, wherein a first data format of the first clinic notes and a second data format of the second clinic notes is based on one or more hardware components or one or more software components of the clinic computing system;

obtain, from a user computing device, a request to generate the electronic medical report, the electronic medical report corresponding to the personal injury of the patient, wherein the request to generate the electronic medical report identifies a context of the electronic medical report as a personal injury context;

automatically generate, in real time, the electronic medical report based on obtaining the request to generate the electronic medical report, wherein to generate the electronic medical report, the electronic medical record module is further configured to at least:

obtain one or more medical reporting standards based on the context of the electronic medical report, wherein the one or more medical reporting standards identify one or more standards for generation of the electronic medical report, dynamically define one or more report structures for generation of the electronic medical report based on the one or more medical reporting standards, wherein the one or more report structures are arranged to define a narrative for the electronic medical report, determine one or more rules from a plurality of rules for the generation of the electronic medical report based on the one or more medical reporting standards, wherein the one or more rules define how to transform at least a portion of the clinic notes based on the one or more medical reporting standards, dynamically map the one or more rules to the one or more report structures to generate an electronic medical report structure, filter the one or more key-value pairs of the patient information to identify a subset of the one or more characteristics of the patient, transform the at least a portion of the clinic notes based on the one or more rules, dynamically generate one or more sentences based at least in part on the filtered one or more key-value pairs and the transformed portion of the clinic notes, and dynamically build the electronic medical report by incorporating the one or more dynamically generated sentences, wherein the electronic medical report satisfies the one or more medical reporting standards, wherein the electronic medical report has a standardized data format, wherein the first clinic notes, the second clinic notes, and the electronic medical report have different data formats;

store the electronic medical report in a data store, the data store storing a plurality of electronic medical reports; and provide, to the user computing device via a network, remote or local access to the electronic medical report based on automatically generating and storing the electronic medical report and verifying that an account associated with the user computing device is authorized to access the electronic medical report.

8. The medical record management system of claim 7, wherein to obtain the clinic notes, the electronic medical record module is further configured to at least:
obtain the first clinic notes from a first clinic computing system; and
obtain the second clinic notes from a second clinic computing system, wherein the first clinic computing system and the second clinic computing system are associated with different clinics.

9. The medical record management system of claim 7, wherein the electronic medical record module is further configured to at least:
verify that a user account associated with the user computing device is authorized to obtain the electronic medical report.

10. The medical record management system of claim 7, wherein the electronic medical record module is further configured to at least:
parse the patient information to identify a subset of the patient information;
generate one or more alerts based on the subset of the patient information; and
configure the one or more alerts to provide one or more indications to a computing device associated with the electronic medical record module.

11. The medical record management system of claim 7, wherein the electronic medical record module is further configured to at least:
parse the patient information to identify a subset of the patient information;
generate one or more alerts based on the subset of the patient information;
configure the one or more alerts to provide one or more indications to a computing device associated with the electronic medical record module;
monitor the patient information; and
cause display of the one or more indications via a display of the computing device based on monitoring the patient information.

12. The medical record management system of claim 7, wherein the electronic medical record module is further configured to at least:
store the one or more rules with a first identifier of the electronic medical report; and
store the one or more report structures with a second identifier of the electronic medical report.

13. The medical record management system of claim 7, wherein the one or more rules comprise one or more extensible stylesheet language transformation rules.

14. The medical record management system of claim 7, wherein the electronic medical report identifies an injury of the patient and one or more of a patient pain level associated with the injury, a type of injury, an area of the injury, or one or more injuries associated with the injury.

15. The medical record management system of claim 7, wherein the electronic medical record module is further configured to at least:
obtain accident information, wherein the electronic medical report identifies the filtered one or more key-value pairs, the transformed portion of the clinic notes, and a transformed portion of the accident information.

16. The medical record management system of claim 7, wherein to dynamically build the electronic medical report, the electronic medical record module is further configured to at least combine a first portion of the clinic notes corresponding to a first clinic and a second portion of the clinic notes corresponding to a second clinic.

17. The medical record management system of claim 7, wherein the electronic medical record module is further configured to at least:
generate a patient profile based on obtaining the patient information;
select an active clinic from a plurality of clinics based on the patient profile, wherein the active clinic is associated with the clinic computing system; and
provide the patient information to the clinic computing system.

18. The medical record management system of claim 7, wherein to obtain the patient information, the electronic medical record module is further configured to at least obtain a first subset of the patient information from the user computing device and a second subset of the patient information from a patient computing device.

19. The medical record management system of claim 7, wherein the electronic medical record module is further configured to at least perform electronic intake of the patient information and the clinic notes.

20. The medical record management system of claim 7, wherein to obtain the medical reporting standards, the electronic medical record module is further configured to at least obtain the medical reporting standards from a computing device associated with a medical reporting standards agency.

21. Non-transitory computer-readable storage media comprising instructions for generation of an electronic medical report satisfying medical reporting standards from clinic notes with different data formats, the instructions executable by a computing system to:
obtain patient information, the patient information comprising one or more key-value pairs, wherein the one or more key-value pairs identify one or more characteristics of a patient;
obtain clinic notes from a clinic computing system via an application programming interface, wherein the clinic notes are associated with the patient, wherein the clinic notes identify one or more of an incident, a medical treatment, or a medical diagnosis associated with a personal injury of the patient, wherein the clinic notes comprise first clinic notes and second clinic notes, wherein the first clinic notes and the second clinic notes have different data formats and comprise a plurality of clinic information, wherein a first data format of the first clinic notes and a second data format of the second clinic notes is based on one or more hardware components or one or more software components of the clinic computing system;

obtain, from a user computing device, a request to generate the electronic medical report, the electronic medical report corresponding to the personal injury of the patient, wherein the request to generate the electronic medical report identifies a context of the electronic medical report as a personal injury context;

automatically generate, in real time, the electronic medical report based on obtaining the request to generate the electronic medical report, wherein to generate the electronic medical report, the non-transitory computer-readable storage media comprises further instructions executable by the computing system to:

obtain one or more medical reporting standards based on the context of the electronic medical report, wherein the one or more medical reporting standards identify one or more standards for generation of the electronic medical report, dynamically define one or more report structures for generation of the electronic medical report based on the one or more medical reporting standards, wherein the one or more report structures are arranged to define a narrative for the electronic medical report, determine one or more rules from a plurality of rules for the generation of the electronic medical report based on the one or more medical reporting standards, wherein the one or more rules define how to transform at least a portion of the clinic notes based on the one or more medical reporting standards, dynamically map the one or more rules to the one or more report structures to generate an electronic medical report structure, filter the one or more key-value pairs of the patient information to identify a subset of the one or more characteristics of the patient, transform the at least a portion of the clinic notes based on the one or more rules, dynamically generate one or more sentences based at least in part on the filtered one or more key-value pairs and the transformed portion of the clinic notes, and dynamically build the electronic medical report by incorporating the one or more dynamically generated sentences, wherein the electronic medical report satisfies the one or more medical reporting standards, wherein the electronic medical report has a standardized data format, wherein the first clinic notes, the second clinic notes, and the electronic medical report have different data formats;

store the electronic medical report in a data store, the data store storing a plurality of electronic medical reports; and provide, to the user computing device via a network, remote or local access to the electronic medical report based on automatically generating and storing the electronic medical report and verifying that an account associated with the user computing device is authorized to access the electronic medical report.

\* \* \* \* \*